(12) United States Patent
Gamache et al.

(10) Patent No.: US 7,931,043 B2
(45) Date of Patent: Apr. 26, 2011

(54) DIAPHRAGM-SEALED VALVE WITH PROCESS PURGING GROOVE

(75) Inventors: Yves Gamache, Adstock (CA); André Fortier, Adstock (CA)

(73) Assignee: Mécanique Analytique Inc., Quebec (CA)

(*) Notice: Subject to any disclaimer, the term of this patent is extended or adjusted under 35 U.S.C. 154(b) by 305 days.

(21) Appl. No.: 12/329,402

(22) Filed: Dec. 5, 2008

(65) Prior Publication Data
US 2009/0152481 A1 Jun. 18, 2009

Related U.S. Application Data

(60) Provisional application No. 60/996,952, filed on Dec. 12, 2007.

(51) Int. Cl.
F16K 31/12 (2006.01)

(52) U.S. Cl. ............... 137/15.04; 137/240; 251/331

(58) Field of Classification Search ........... 137/15.04, 137/240, 312; 251/331
See application file for complete search history.

(56) References Cited

U.S. PATENT DOCUMENTS

| | | | |
|---|---|---|---|
| 3,085,440 A | 4/1963 | Guenther | |
| 3,111,849 A | 11/1963 | Broerman | |
| 3,139,755 A | 7/1964 | Reinecke et al. | |
| 3,140,615 A | 7/1964 | Broerman | |
| 3,198,018 A | 8/1965 | Broerman | |
| 3,376,894 A | 4/1968 | Broerman | |
| 3,387,496 A | 6/1968 | Broerman | |
| 3,417,605 A | 12/1968 | Hahn | |
| 3,439,542 A | 4/1969 | McCray | |
| 3,492,873 A | 2/1970 | Broerman et al. | |
| 3,545,491 A | 12/1970 | Broerman | |
| 3,633,426 A | 1/1972 | Broerman | |
| 4,112,766 A | 9/1978 | Ragains | |
| 4,276,907 A | 7/1981 | Broerman | |
| 4,333,500 A | 6/1982 | Broerman | |
| 5,601,115 A | 2/1997 | Broerman | |
| 6,202,698 B1 | 3/2001 | Stearns | |
| 6,216,739 B1 * | 4/2001 | Fukushima et al. | 137/613 |
| 6,907,897 B2 * | 6/2005 | Maula et al. | 251/331 |
| 2006/0042686 A1 | 3/2006 | Gamache et al. | |

* cited by examiner

Primary Examiner — Kevin L Lee
(74) Attorney, Agent, or Firm — Fitzpatrick, Cella, Harper & Scinto

(57) ABSTRACT

A diaphragm-sealed valve provided with a valve cap and a valve body, a diaphragm and a plunger assembly. The diaphragm is compressibly positioned between the valve cap and the valve body. The valve body comprises a process purging channel extending along a main recess of the valve body, under a pre-formed deformation of the diaphragm. A process purging inlet passage and a process purging outlet passage, both opening on the process purging channel, allow for a purging gas to flow in the process purging channel.

16 Claims, 24 Drawing Sheets

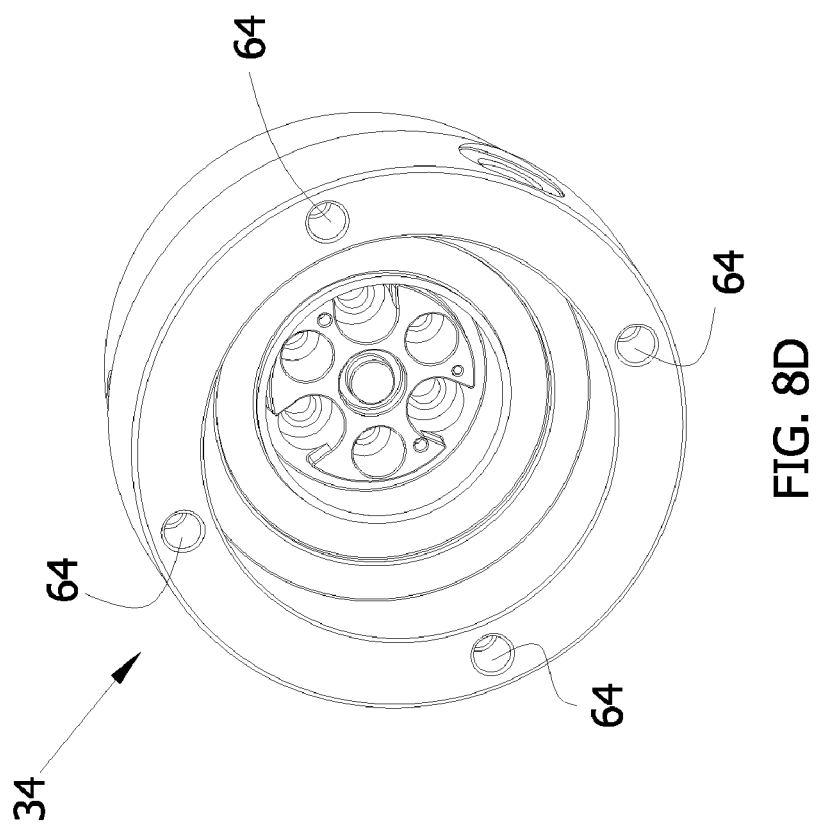
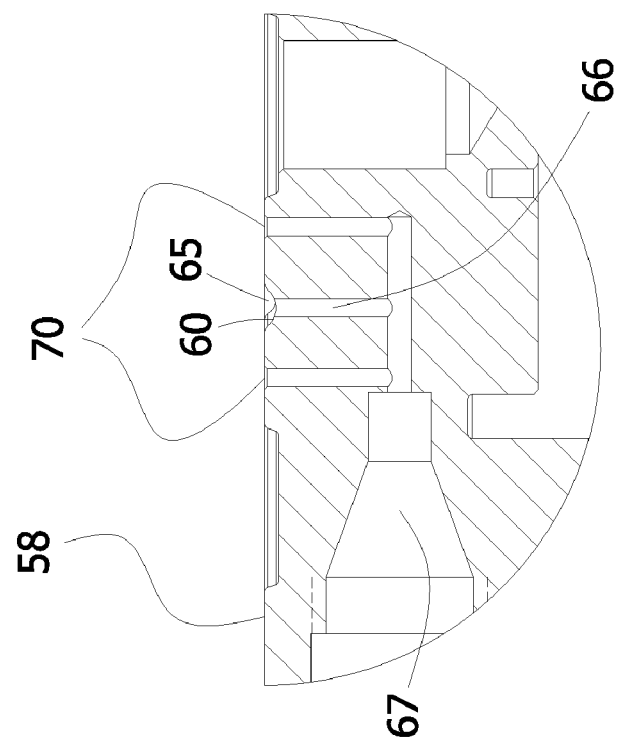
FIG. 8D
FIG. 8C

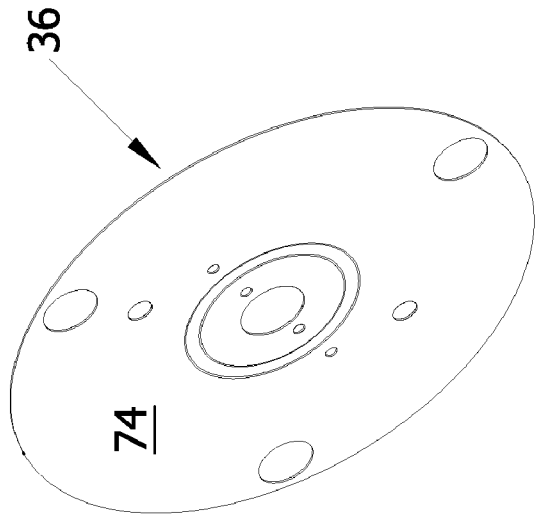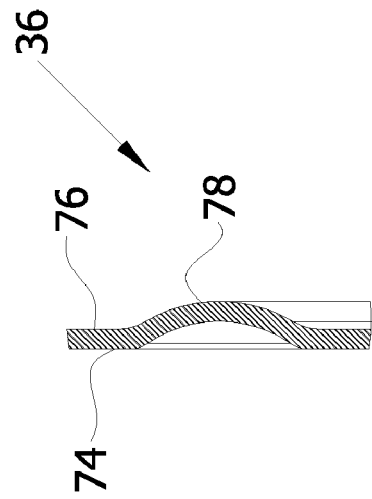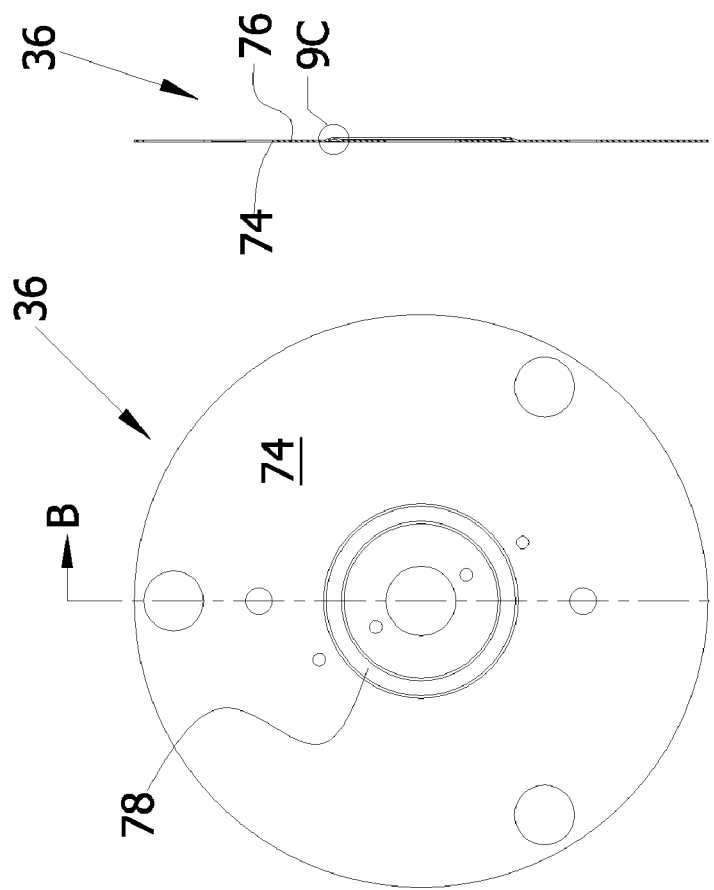
FIG. 9A  FIG. 9B  FIG. 9C  FIG. 9D

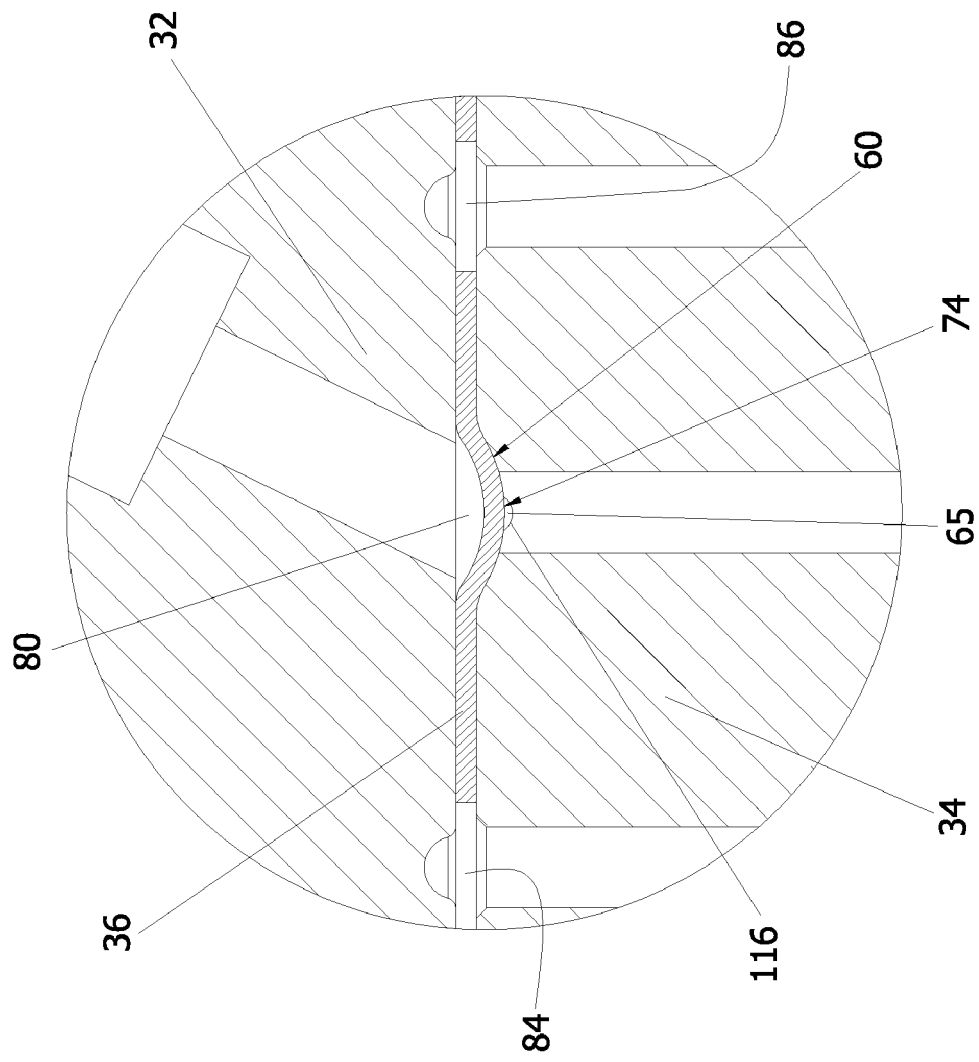
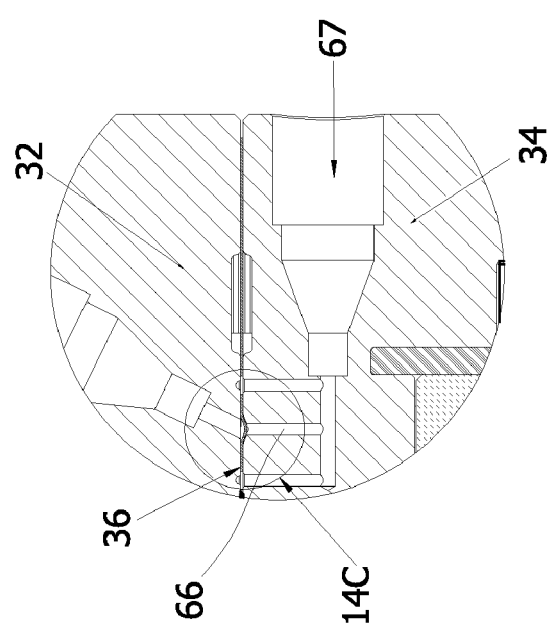
FIG. 14C
FIG. 14B

DIAPHRAGM-SEALED VALVE WITH PROCESS PURGING GROOVE

FIELD OF THE INVENTION

The present invention generally relates to fluid analytical systems and more particularly concerns a diaphragm-sealed valve having a process purging groove.

BACKGROUND OF THE INVENTION

As well known by people involved in the art, chromatographic systems rely on the use of valves to allow reproducible sample introduction and various column switching schemes.

For the last forty years, many people have designed diaphragm valves for chromatography. Such diaphragm valves have been used in many commercially available gas chromatographs. They are apt to be integrated more easily in a gas chromatograph due to their physical size and since the actuator is embedded in the valve itself. These characteristics make them attractive for gas chromatograph manufacturers.

Referring to FIG. 1 (PRIOR ART), there is shown an example of a typical diaphragm-sealed valve as known in the art. The valve 1 is provided with a top block 2 having an interface 4 and a plurality of ports 6. Each of the ports 6 opens at the interface 4 and has an inclined thread passage 8 to connect various analytical fitting and tubing (not shown). At the bottom of the inclined thread passage 8, there is a conduit 10 extending in the top block 2 and opening at the interface 4. The ports 6 are arranged on a circular line on the interface 4 of the top block 2. The interface 4 is advantageously flat and polished to minimize leaks between ports and from the ambient atmosphere. The valve 1 is also provided with a bottom block 12 and a diaphragm 14, which is generally made of polyimide, Teflon or other polymer material. The diaphragm 14 is positioned between the top block interface 4 and the bottom block 12, and has a recess therein extending along the circular line formed by the ports 6 and biased away from the interface 4 of the top block 2. The recess 18 in the diaphragm 14 sits in a matching recess 20 made in the bottom block 12, thereby allowing some clearance for fluid circulation between adjacent ports 6.

The valve 1 is also provided with a plurality of plungers 16 mounted in the bottom block 12, each being respectively arranged to be able to compress the diaphragm 14 against the top block 2 at a position located between two of the ports 6. Preferably, as illustrated, when the valve is at rest, three plungers 16 are up while the other three are down. When the plungers are up, they compress the diaphragm 14 against the top block 2 and close the conduits made by the diaphragm recess 18, so that fluid circulation is blocked. The bottom block 12 keeps the plungers 16 and the actuating mechanism in position.

The performance of valves of the type shown in FIG. 1 is generally poor. The leak rate from port to port is too high for most applications and thus limits the system performance. Moreover, the pressure drop on the valve's ports differs from port to port, causing pressure and flow variations in the system. This causes detrimental effects on column performance and detector baseline. Furthermore, many valve designs allow for unacceptable inboard contamination.

Known prior art includes many variations of the valve shown in FIG. 1 (PRIOR ART) attempting to prevent or minimize inboard and outboard contamination and generally improve the performance of diaphragm valves.

However, one drawback still not resolve is the contamination of process gas by ambient air or light gas located between the under surface of the diaphragm 14 and the upper surface of the bottom block 12. The gas located underneath the diaphragm 14 mainly comes from the activation of the plungers 16, and may also be due to inboard leaks. The gas located underneath the diaphragm 14 permeates upwardly through it into the recess 18 and thereby contaminates the process gas circulating in the recess 18. This problem more frequently occurs in application in which light gas is used, such as helium or hydrogen. In other situations, hazardous process gas, such as silane, may leak or diffuse through the diaphragm and damage the valve.

Another drawback of existing design is the difficulty to operate such valves when used in sub-atmospheric applications, or in high pressure applications, for example when pressures in the order of thousands of pounds per squared inch are applied. When such high pressures are used, the diaphragm is pressed downwardly into the matching recess 20 in the bottom block 12, and it becomes difficult for the plungers 16 to compress the diaphragm upwardly against the interface 4 of the top block 2.

There is therefore a need for an improved diaphragm-sealed valve.

SUMMARY OF THE INVENTION

In accordance with a first aspect of the present invention, there is provided a valve that includes a valve cap having a first interface and a plurality of process conduits extending therethrough, each process conduit ending in a process port opening at the first interface. The valve also includes a valve body having a second interface facing the first interface of the valve cap, the second interface being provided with a main recess aligned with said process ports, the valve body being provided with a plurality of passages each extending in the valve body and opening in the main recess between two of the process ports. The valve also includes a diaphragm having a first surface facing the valve cap and a second surface facing the valve body. The diaphragm is compressibly positioned between the first and the second interfaces and has a pre-formed deformation lying in the main recess of the valve body. The first surface of the diaphragm defines with the first interface of the valve cap a communication channel between the process ports. The valve also includes a plunger assembly having a plurality of plungers, each placed in one of said passages and being slideable therein between a closed position where the plunger projects towards the first interface pressing the diaphragm against the first interface of the valve cap between two adjacent ports for interrupting communication there between, and an open position where the plunger is retracted within the valve body, extending away from the diaphragm for allowing communication between the two adjacent ports. The valve body further comprises a process purging channel extending along the main recess under the pre-formed deformation of the diaphragm, a process purging inlet passage and process purging outlet passage, both opening on the process purging channel.

In accordance with a second aspect of the present invention, there is also provided a method for collecting leaks from a communication channel in a valve. The valve includes a valve cap having a first interface and a plurality of process conduits extending therethrough, each process conduit ending in a process port opening at the first interface. The valve also includes a valve body having a second interface facing the first interface of the valve cap, the second interface being provided with a main recess. The valve body is further provided with a plurality of passages each extending in the valve body and opening in the main recess between two of the process ports. The valve also includes a diaphragm having a first surface facing the valve cap and a second surface facing the valve body. The diaphragm is compressibly positioned between the first and the second interfaces and has a pre-formed deformation lying in the main recess of the valve body, the first surface of the diaphragm defining with the first interface of the valve cap the communication channel between the process ports. The valve also includes a plunger assembly having a plurality of plungers, each placed in one of the passages and being slideable therein between a closed position where the plunger projects towards the first interface pressing the diaphragm against the first interface of the valve cap between two adjacent ports for interrupting communication there between, and an open position where the plunger is retracted within the valve body, extending away from the diaphragm for allowing communication between the two adjacent ports. The method includes the steps of:

a) providing the valve body with a process purging channel extending along the main recess under the pre-formed deformation of the diaphragm, a process purging inlet passage and a process purging outlet passage, both opening on the process purging channel;
  b) circulating purging gas in the process purging channel from the process purging inlet passage to the process purging outlet passage.

BRIEF DESCRIPTION OF THE DRAWINGS

These and other features and advantages of the invention will become apparent upon reading the detailed description and upon referring to the drawings in which:

FIG. 8C is an enlarged view of section 8C of FIG. 8B. FIG. 8D is a bottom perspective view of the valve body of FIG. 8A.

FIG. 9A is a top view of the diaphragm of the valve of FIG. 2, according to a preferred embodiment of the present invention. FIG. 9B is a cross-sectional side view of the diaphragm along line B-B of FIG. 9A. FIG. 9C is an enlarged view of section 9B of FIG. 9B. FIG. 9D is a perspective view of the diaphragm of FIG. 9A.

FIG. 10C is a bottom view of the push plate of FIG. 10A while

FIG. 11A is a bottom perspective view of the normally open piston of the valve of FIG. 2, according to a preferred embodiment of the present invention, while

FIG. 12A is a bottom perspective view of the normally closed piston of the valve of FIG. 2, according to a preferred embodiment of the present invention, while

FIG. 12A is a bottom perspective view of the normally closed piston of the valve of FIG. 2, according to a preferred embodiment of the present invention, while

FIG. 14B is an enlarged view of section 14B of FIG. 14A. FIG. 14C is an enlarged view of section 14C of FIG. 14B.

Figure 1:
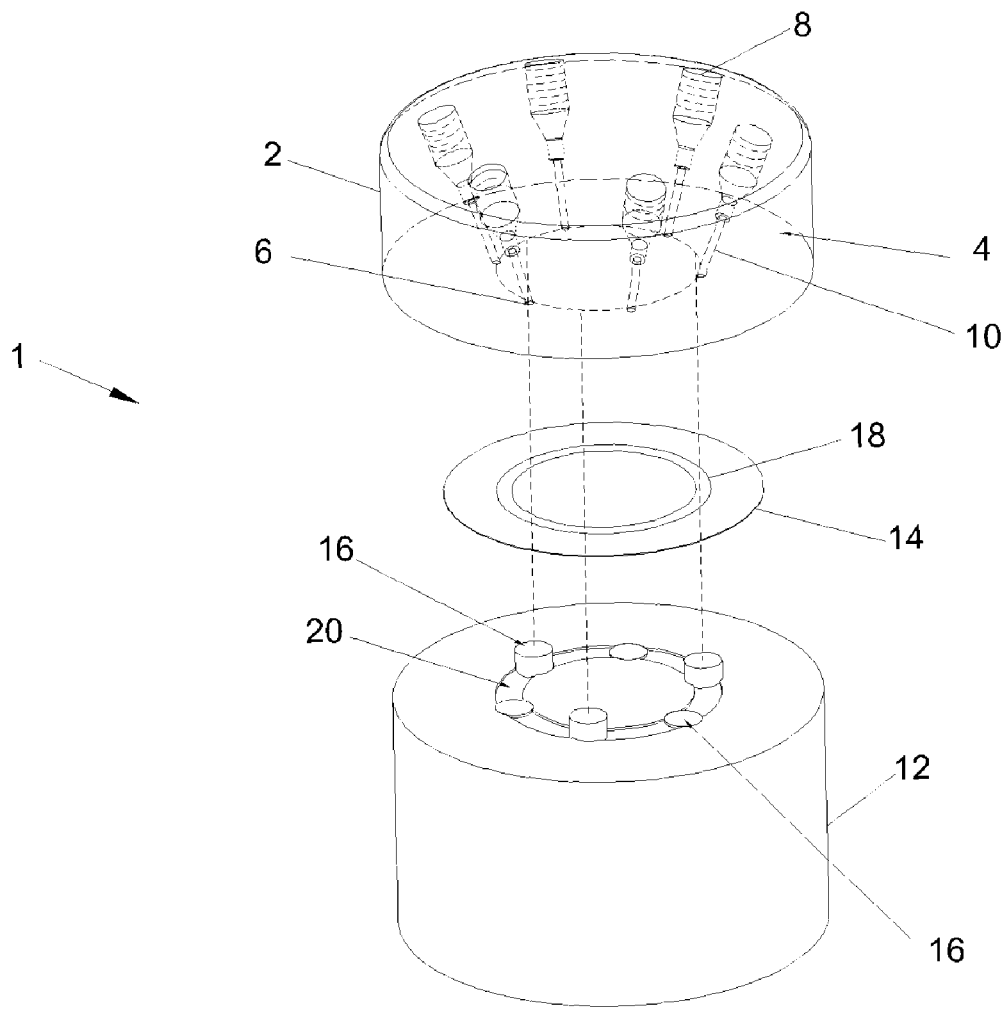
FIG. 1 (PRIOR ART) is an exploded perspective view of a diaphragm-sealed valve known in the art, in partial transparency.

While the invention will be described in conjunction with example embodiments, it will be understood that it is not intended to limit the scope of the invention to such embodiments. On the contrary, it is intended to cover all alternatives, modifications and equivalents as may be included as defined by the present application.

DESCRIPTION OF PREFERRED EMBODIMENTS

In the following description, similar features in the drawings have been given similar reference numerals. To preserve the clarity of the drawings, some references numerals have been omitted, if they were already identified in a preceding figure.

Referring to FIGS. 2 and 4 to 6, there is shown a valve 30 according to a preferred embodiment of the present invention.

The valve 30 is of the diaphragm-sealed type valve. Such a valve may be used in analytical equipments of various types, and more particularly chromatographic equipments or online analyzers.

As illustrated in all of these figures, the valve 30 includes four main elements: a valve cap 32, a valve body 34, a diaphragm 36 compressibly positioned between the valve cap 32 and the valve body 34, and a plunger assembly 38. The valve 30 may also include a bottom cap 40 or other equivalent structure holding the plunger assembly 38 to the valve body 34. In accordance with an aspect of the present invention, the valve 30 is also provided with features for collecting leaks which may occur during operation, as will be explained in more detail further below.

Valve Cap

Figure 4:
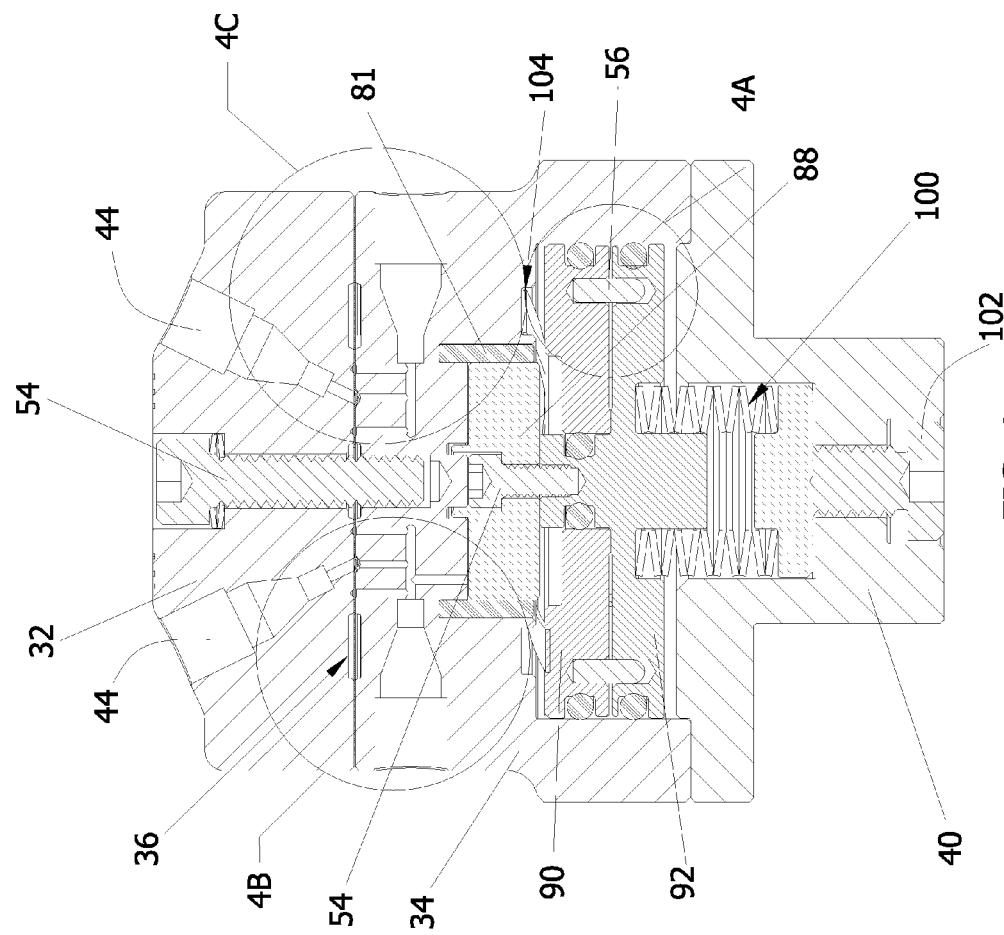
FIG. 4 is a cross-sectional side view of a diaphragm-sealed valve along line IV-IV of FIG. 3, according to a preferred embodiment of the invention.
Figure 5:
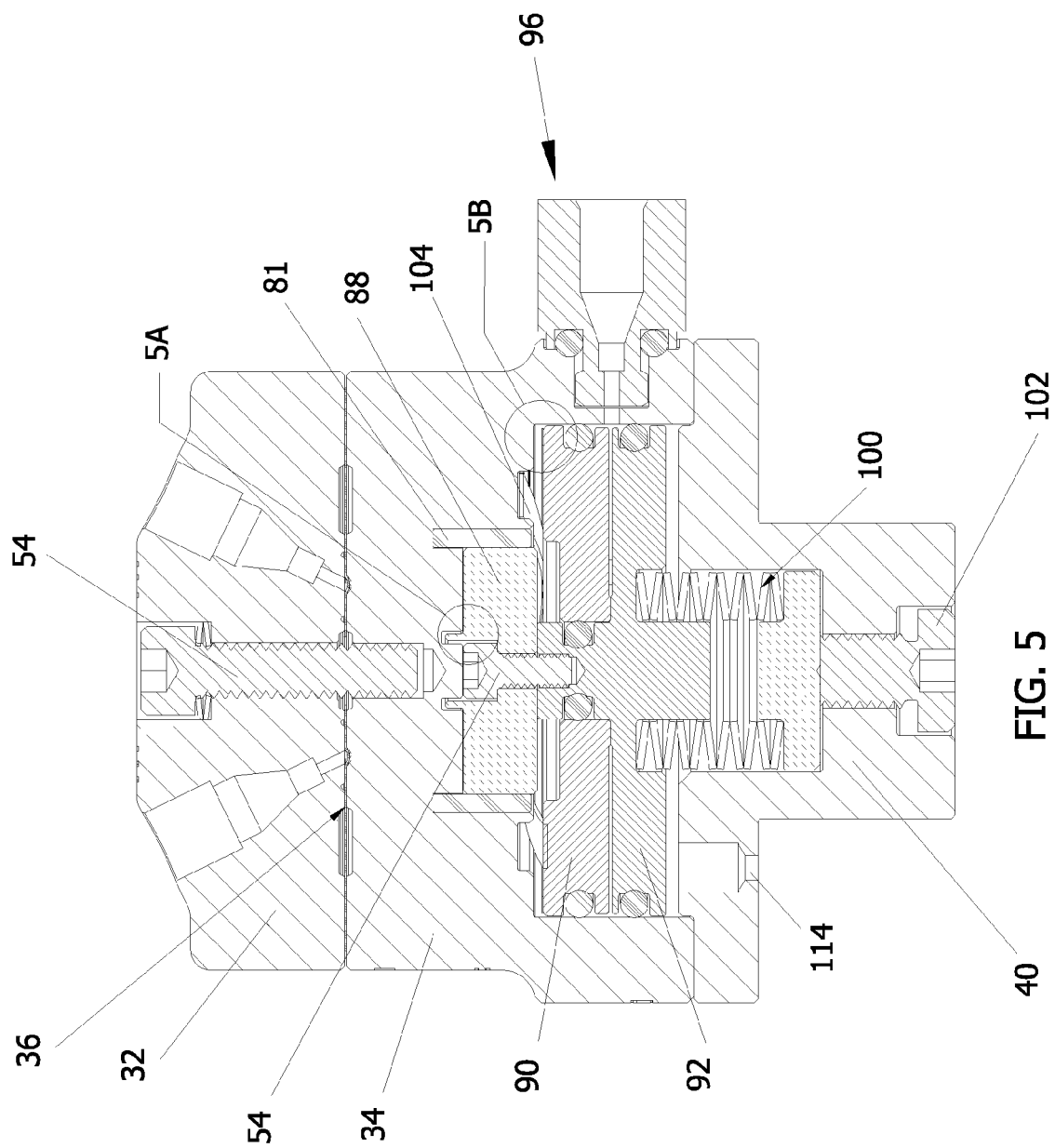
FIG. 5 is a cross-sectional side view of a diaphragm-sealed valve along line V-V of FIG. 3.
Figure 5B:
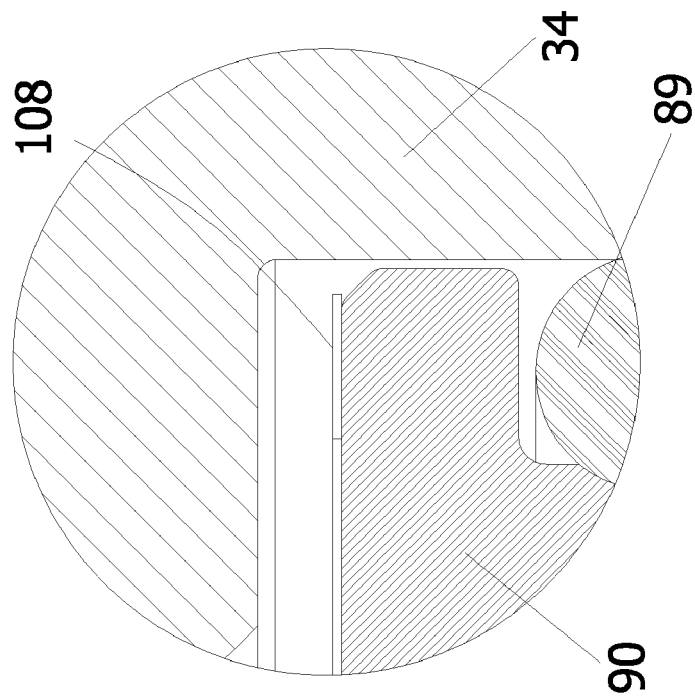
FIG. 5B is an enlarged view of section 5B of FIG. 5.
Figure 5A:
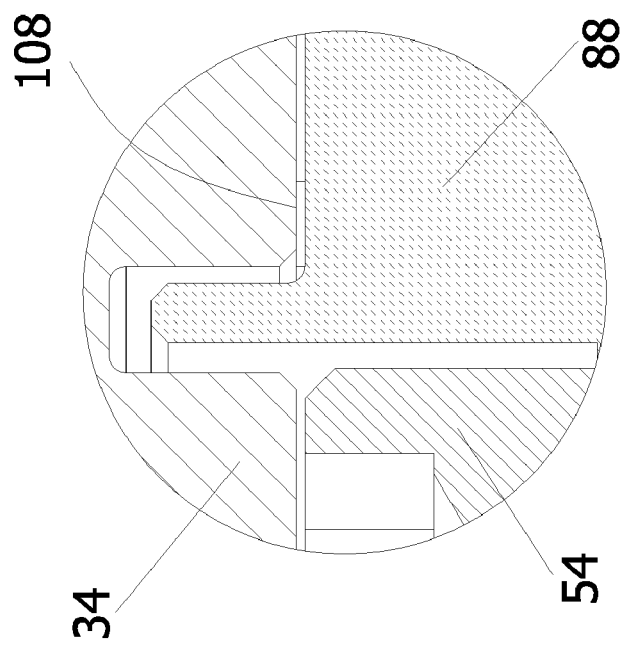
FIG. 5A is an enlarged view of section 5A of FIG. 5.
Figure 6:
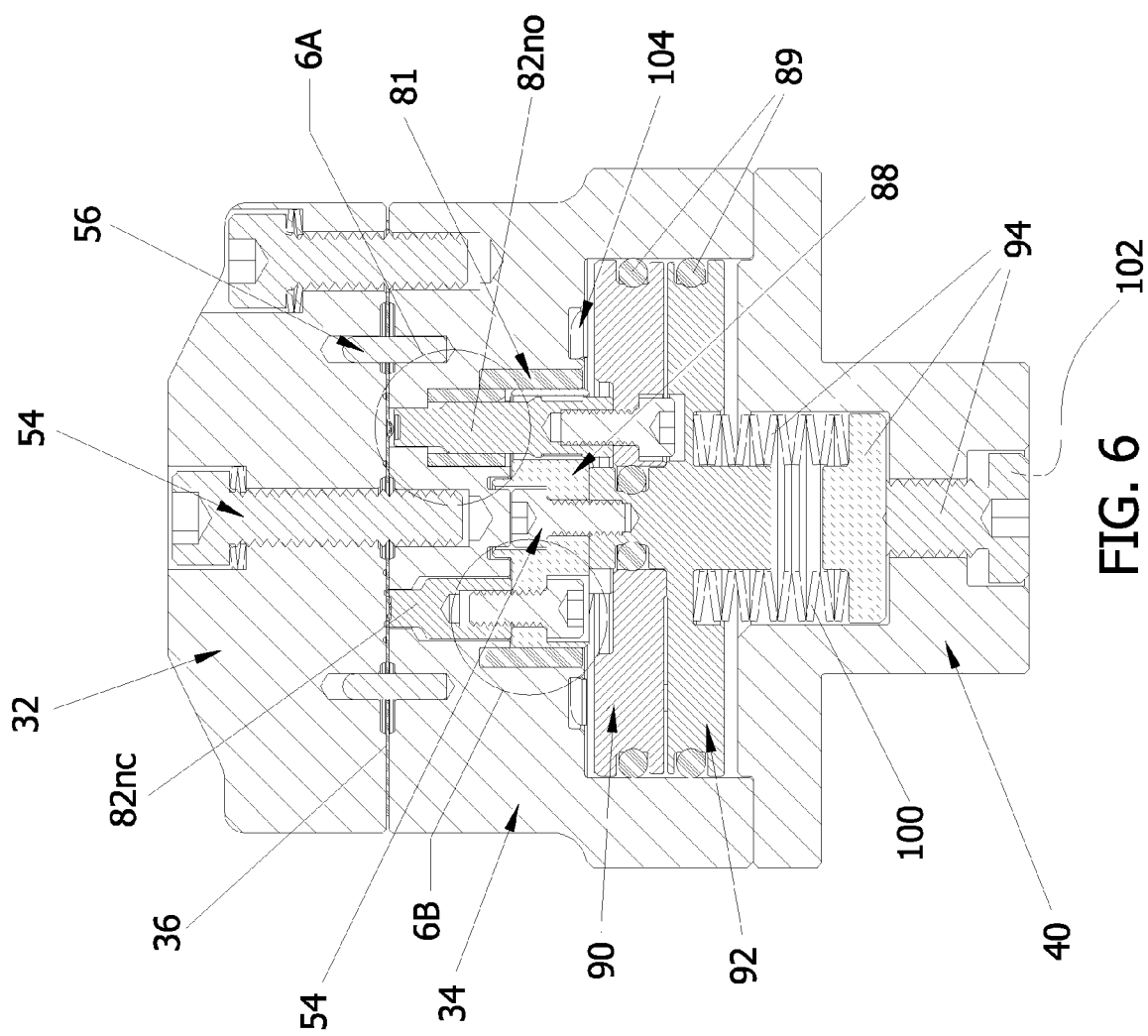
FIG. 6 is a cross-sectional side view of a diaphragm-sealed valve along line VI-VI of FIG. 3.
Figure 6B:
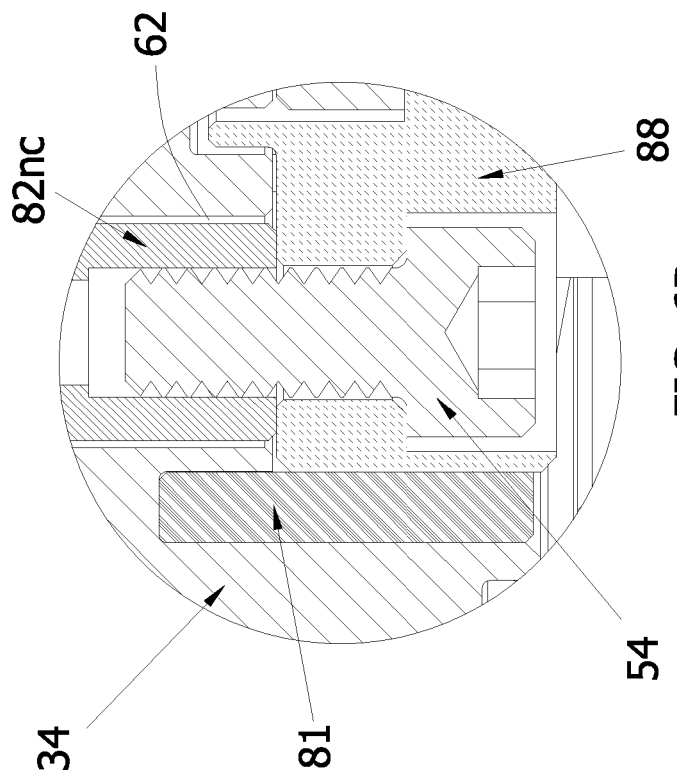
FIG. 6B is an enlarged view of section 6B of FIG. 6.
Figure 6A:
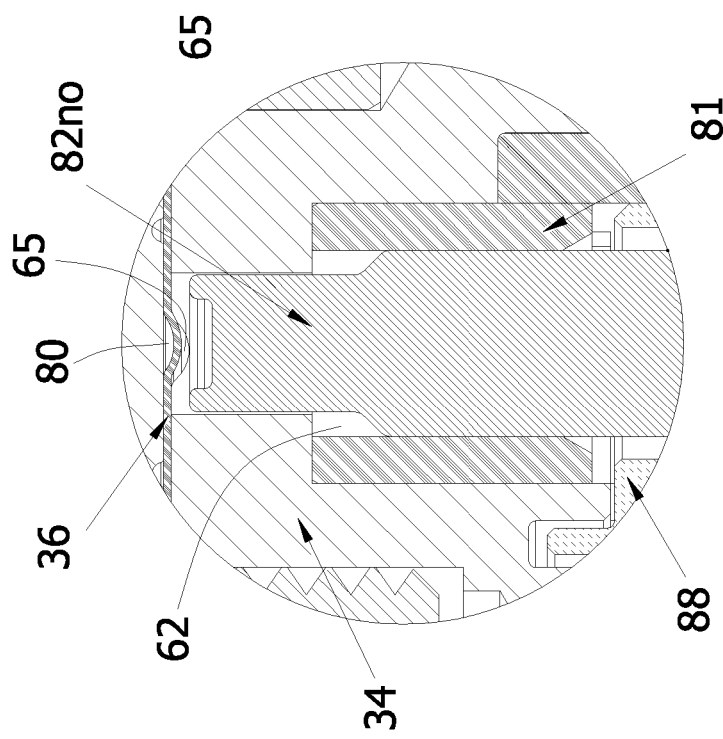
FIG. 6A is an enlarged view of section 6A of FIG. 6.

Still referring to FIGS. 2 and 4 to 6, and more clearly shown in FIGS. 7A to 7E, the valve cap 32 has an interface, hereinafter referred to as the first interface 42, and a plurality of process conduits 44 extending through it. This first interface 42 is flat and smooth, and is in contact with the diaphragm 14 when the valve is assembled (as shown in FIGS. 4 to 6). Each process conduit 44, in this preferred embodiment amounting to six (6), ends in a process port 46 opening at the first interface 42. The process ports 46 are preferably circularly arranged on the first interface 42. Best shown in FIG. 7C, each of the process conduits 44 are preferably formed by a larger threaded hole 48 for receiving tubing connections and a smaller fluid passage 50 ending in the process port 46. In this embodiment, the valve cap 32 has a cylindrical shape and is for example made of electro-polished stainless steel. The valve cap 32 is also provided with screw holes 52 for receiving socket head cap screws 54 (shown in FIG. 2), for holding the valve cap 32 to the valve body 34. The alignment of the valve cap 32 with the valve body 34 is ensured by dowel pins 56 (also shown in FIG. 2). Of course, other arrangements for holding the valve cap 32 to the valve body 34 can be considered. Optionally, a layer of polymer covers the first interface 42 of the valve cap 32. Other materials, for example ceramic or various types of polymers, may be used as material for the valve cap 32. Shapes other than a cylindrical one may also be considered. Of course, other embodiments of the valve cap may include 4, 8, 10, 12 or any other convenient number of process ports.

Valve Body

Figure 2:
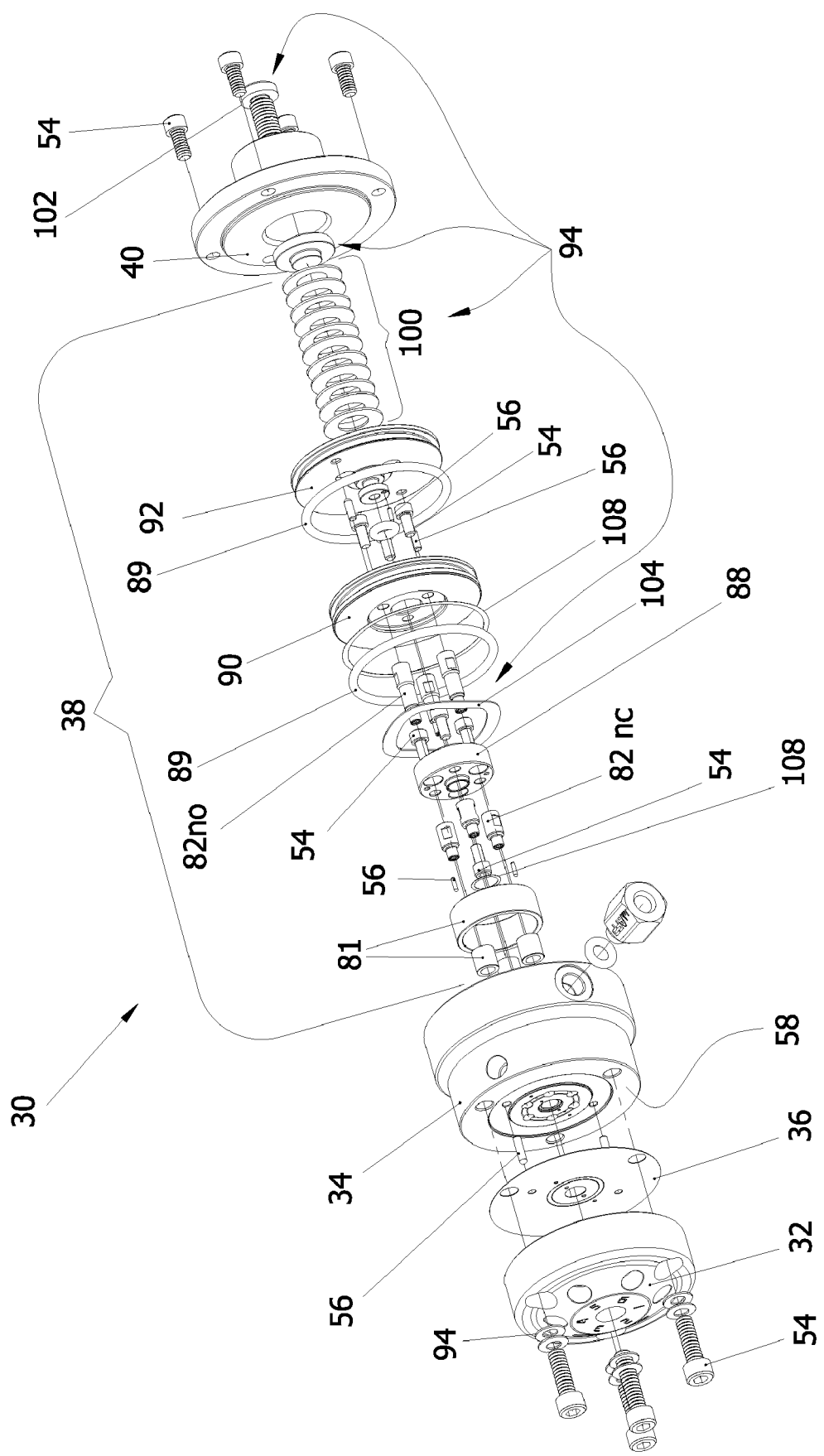
FIG. 2 is an exploded perspective view of a diaphragm-sealed valve according to an embodiment of the invention.
Figure 3:
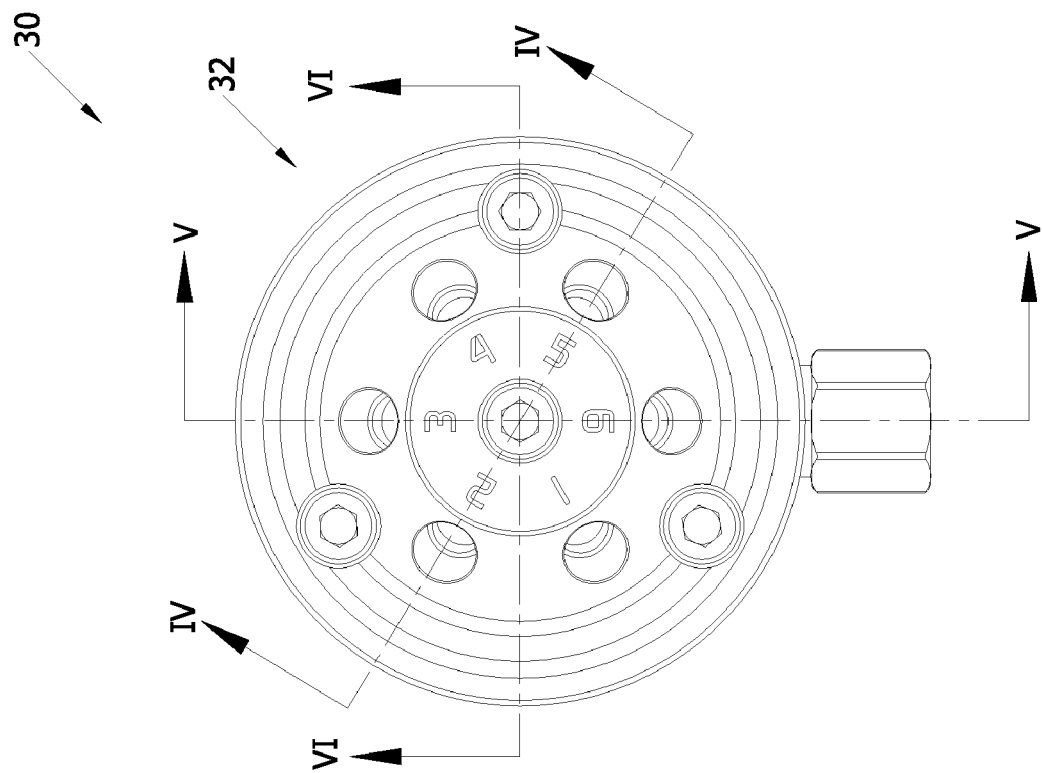
FIG. 3 is a top view of a diaphragm-sealed valve according to the present invention.

Now referring to FIGS. 8A to 8G, there is shown a preferred embodiment of the valve body 34 of the valve 30. Such as for the valve cap 32 described above, the valve body 34 also has an interface, hereinafter referred to as the second interface 58, which faces the first interface 42 of the valve cap when the valve is assembled (as shown in FIGS. 4 to 6). Just as the first interface 42 of the valve cap 32, it is smooth and flat. The second interface 58 is provided with a main recess 60, preferably having a circular outline and it is aligned with the process ports 46 of the valve cap 32 when the valve elements are assembled and the valve is ready for use, as in FIGS. 4 to 6. The valve body 34 also includes a plurality of passages 62 (more clearly shown in FIG. 8F) each extending in the valve body 34 and opening at one end in the main recess 60 between two of the process ports 46. The other ends of the passages 62 open in a valve body cavity 63 which is for housing the plunger assembly 38 (as shown in FIG. 2). The valve body is also provided with a first set of screw holes 64 for receiving the socket head cap screws 54 that hold the valve body to the valve cap (best shown in FIG. 8A) and a second set of screw holes 64 for receiving the socket head cap screws 54 that hold the valve body 34 to the bottom cap 40 (best shown in FIG. 8D). Of course, other arrangements could be considered for affixing the valve body 34 to the bottom cap 40.

Diaphragm

Figure 4B:
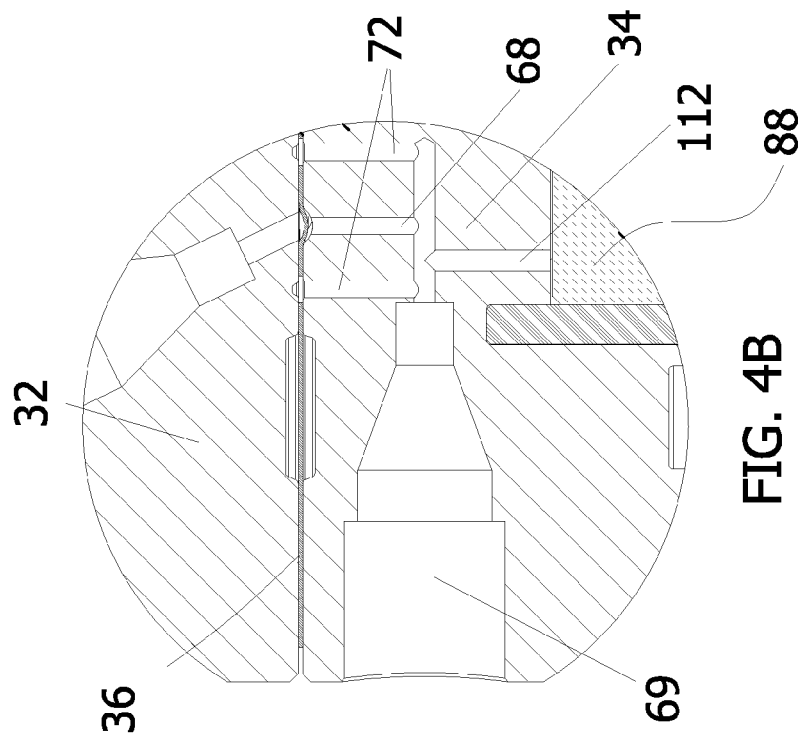
FIGS. 4A, 4B and 4C are enlarged views of sections 4A, 4B, 4C of FIG. 4.
Figure 4A:
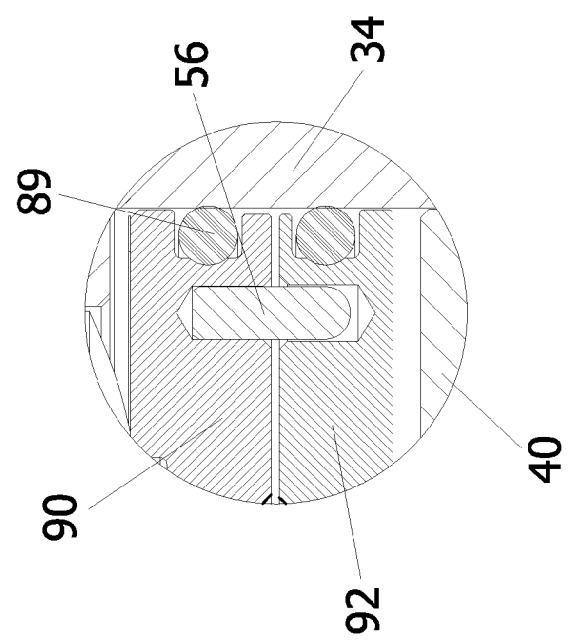
Figure 4D:
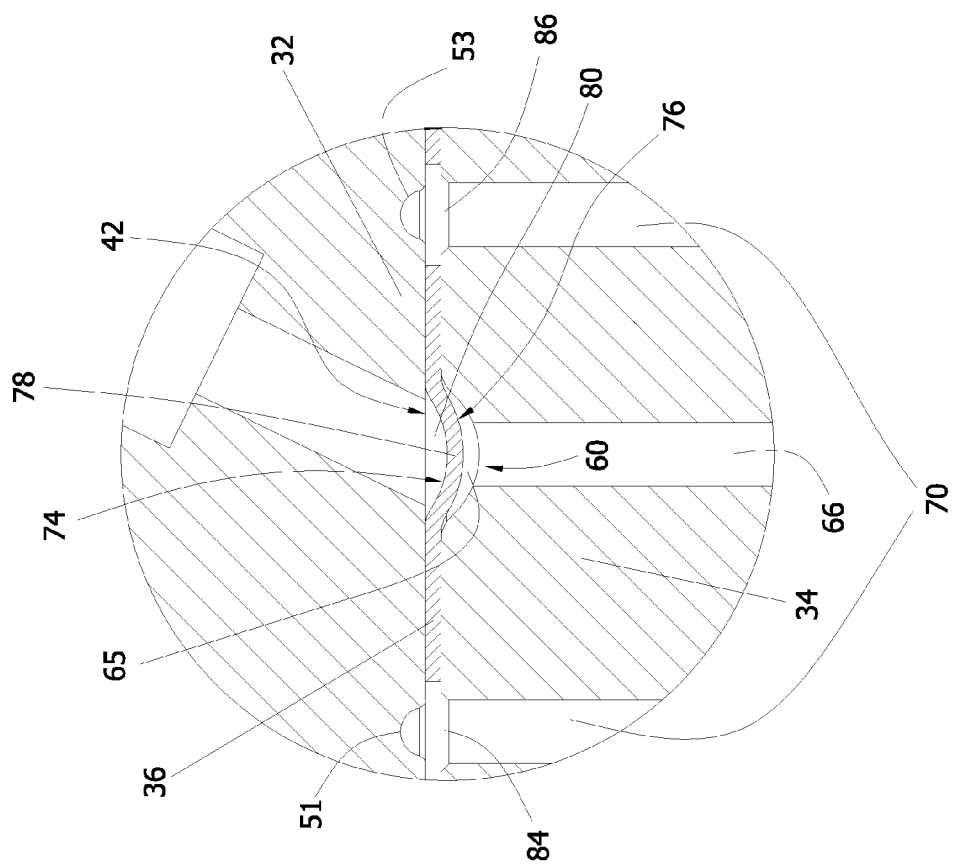
FIG. 4D is an enlarged view of section 4D of FIG. 4C.
Figure 4C:
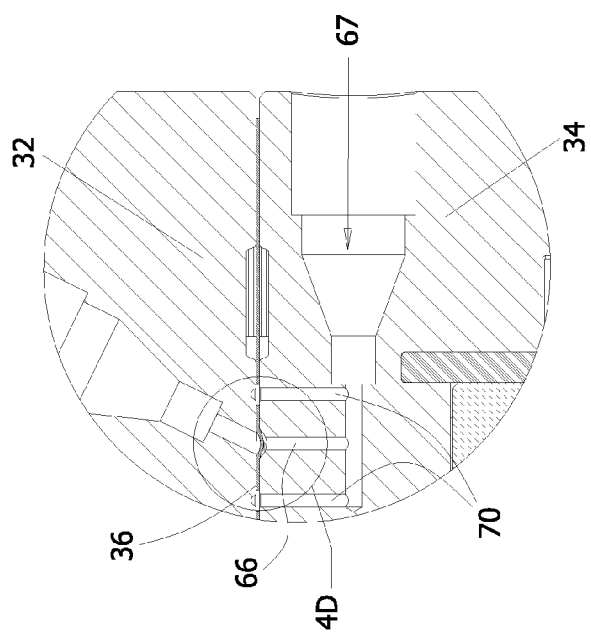

Now referring to FIGS. 2, 4D and also to FIGS. 9A to 9C, there is shown a preferred embodiment of the diaphragm 36 of the valve 30. The diaphragm 36 has a first surface 74 facing the valve cap 32 and a second surface 76 facing the valve body 34, the diaphragm 36 being compressibly positioned between the first 42 and the second 58 interfaces when the valve is assembled and ready for use (as in FIGS. 4 to 6). As more clearly shown in FIG. 4D, the diaphragm has a pre-formed deformation 78 lying within the main recess 60 of the valve body 34, the first surface 74 of the diaphragm 36 defining with the first interface 42 of the valve cap 32 a communication channel 80 between the process ports.

The diaphragm 36 can be made of multiple layers of polymer, with or without a thin metallic layer, or alternatively be made of metal only. Metals that may be used are stainless steel 316, aluminium, chrome-nickel alloy, copper and the like. For applications requiring high gas-tightness sealing, a diaphragm 36 made of multiple layers of polymer is preferably used, while other applications require a thin metallic layer over the polymer layers.

Leaks Collection

The various features of the valve allowing the collection of leaks at the first and second interfaces will now be described in more detail.

Figure 8B:
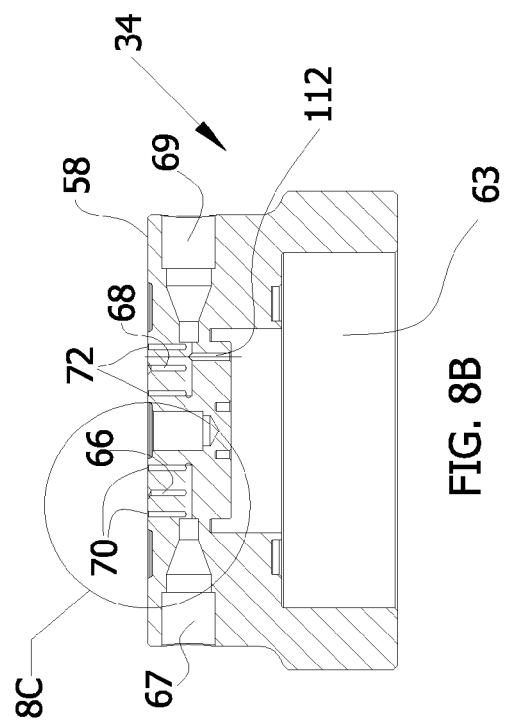
FIG. 8B is a cross-sectional side view of the valve body along line B-B of FIG. 8A.
Figure 8A:
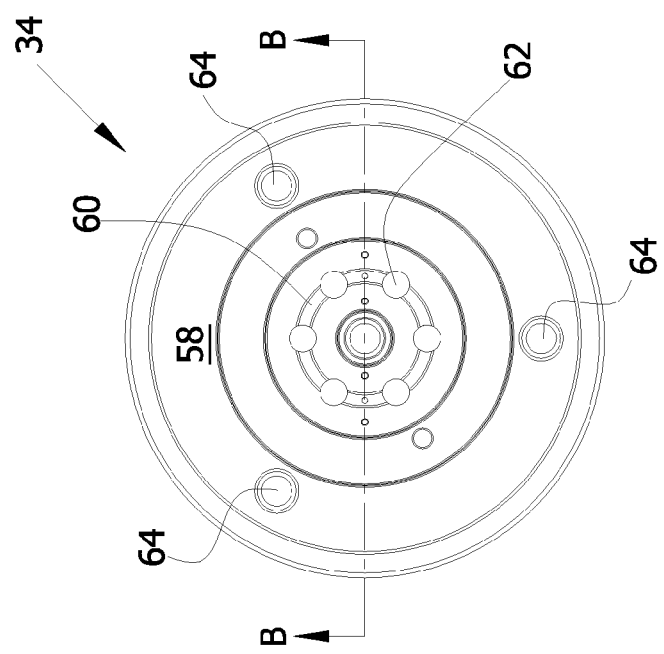
FIG. 8A is a top view of the valve body of the valve of FIG. 2, according to a preferred embodiment of the present invention.
Figure 8F:
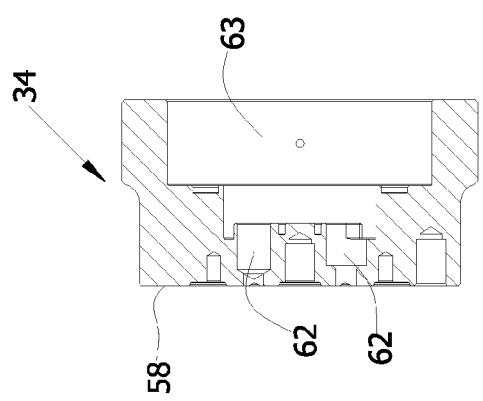
FIGS. 8F and 8G are cross-sectional side views of the valve body along line F-F and G-G of FIG. 8E, respectively.
Figure 8H:
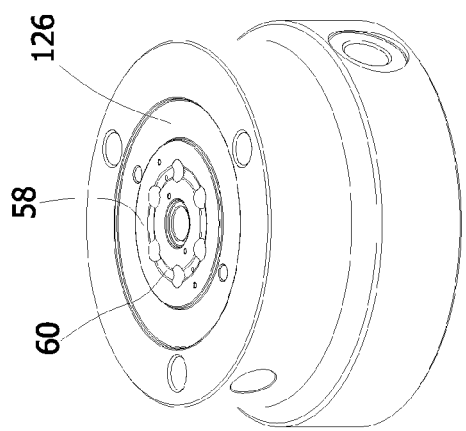
FIG. 8H is a top perspective view of the valve body of FIG. 8A.
Figure 8E:
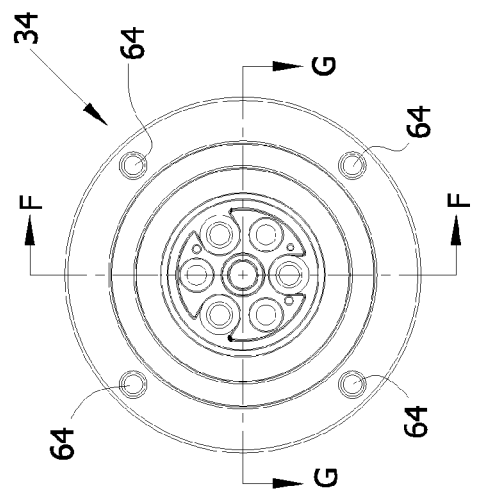
FIG. 8E is a bottom view of the valve body of FIG. 8A.
Figure 8G:
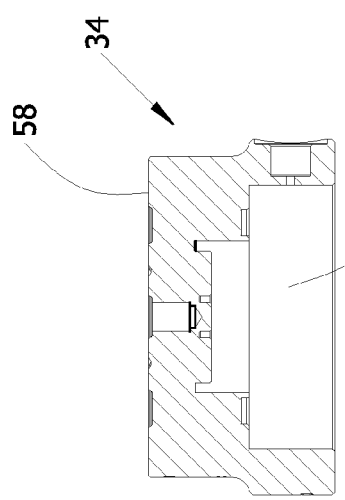

Best shown in FIGS. 8B and 8C, the valve body 34 is also provided with a process purging channel 65 extending along the main recess 60, a process purging inlet passage 66 and process purging outlet passage 68. The process purging inlet passage 66 is connected to an entry 67 of a purge line, and the process purging outlet passage 68 is connected to an exit 69 of a purge line. Preferably, the process purging inlet passage 66 and the process purging outlet passage 68 are diametrically opposed along the main recess 60, but other configuration can be considered. Still preferably, the valve body 34 is further provided with a pair of fluid inlets 70 and a pair of fluid outlets 72, the pair of fluid inlets 70 also being connected to the entry 67 of a purge line, and the pair of fluid outlets 72 being connected the exit 69 of the purge line. Better shown in FIGS. 4B and 8B, the valve body 34 may be provided with a actuation purging outlet passage 112, extending in the valve body 34 and located opposite to the push plate 88 of the plunger assembly 38, between the cavity 63 and the exit of the purge line, for preventing pressure build up in the cavity 63, above the piston 90 (as shown in FIG. 4).

Now referring to FIGS. 4 and 4B to 4D, the process purging channel 65 extends along the main recess 60, under the pre-formed deformation 78 of the diaphragm 36. As more clearly shown in FIG. 4D, the process purging channel 65 is defined by the second surface 76 of the diaphragm and the main recess 60, the process purging channel having a semi-circular cross-section. Since the radius of the main recess 60 is greater than the radius of the pre-formed deformation 78 of the diaphragm 36, the space created defines the process purging channel 65.

In use, a purging gas enters through the entry 67 of the purge line, then flows in the process purging inlet passage 66, and then circulates into the process purging channel 65. The purging gas then flows out to the process purging outlet passage 68 and finally exits through the exit 69 of the purge line. This process purging channel 65 combined with the process purging inlet 66 and outlet 68 advantageously allows evacuating ambient air or gas located underneath the diaphragm, that may otherwise diffuse through the diaphragm and contaminate the process gas circulating in the communication channel 80. Gas may also be injected in the purging inlet 66 at a specific pressure and circulated in the channel 65 and out of the valve through the outlet 68, in order to balance the pressures applied over and under the diaphragm 36.

Figure 14A:
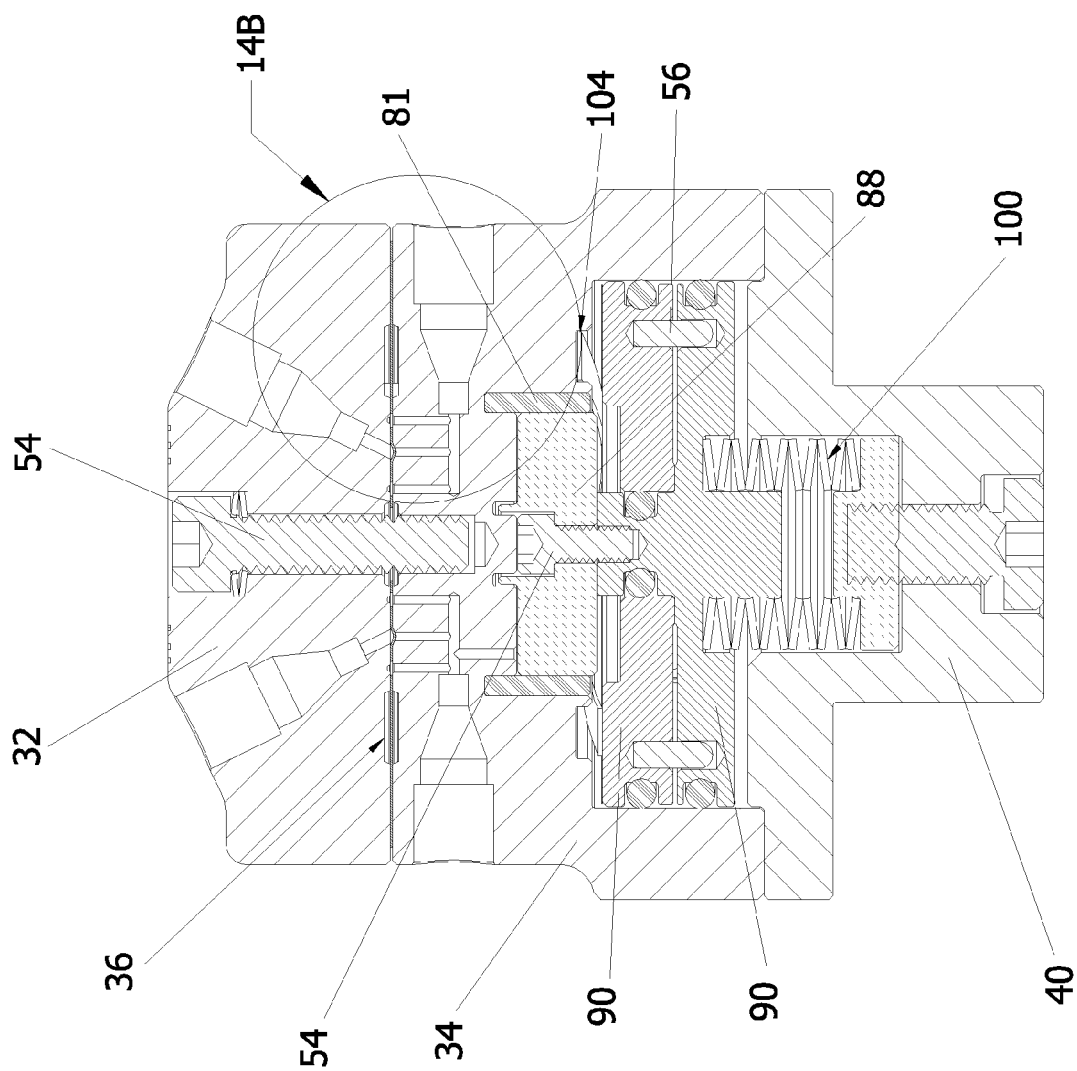
FIG. 14A is a cross-sectional side view of a diaphragm-sealed valve along line IV-IV of FIG. 3, according to another preferred embodiment of the invention.
Figure 15B:
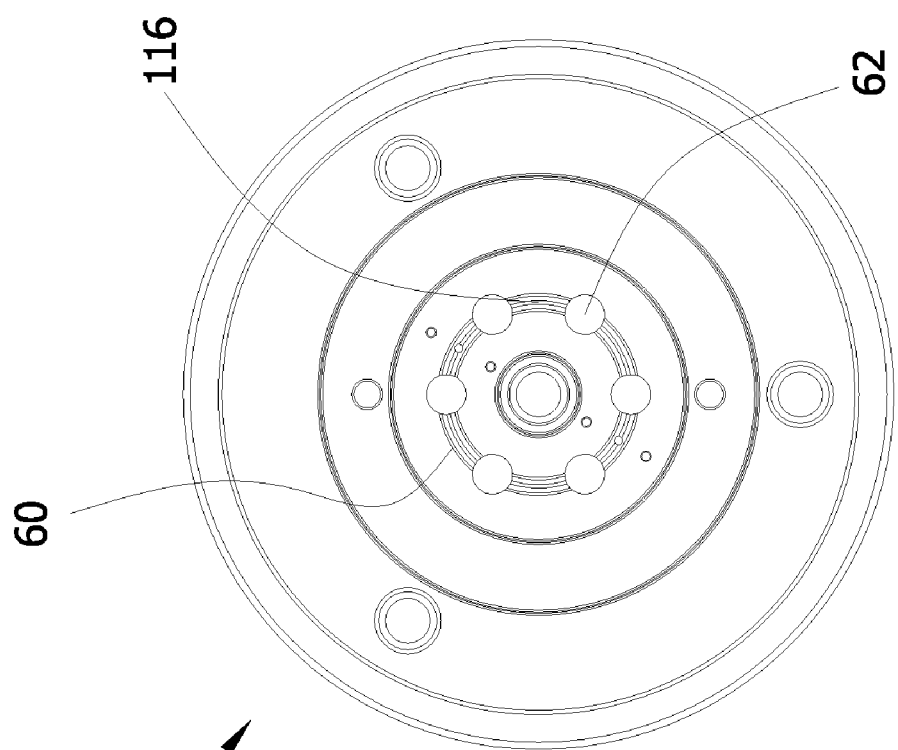
FIG. 15B is a top perspective view of the valve body of FIG. 15A.
Figure 15A:
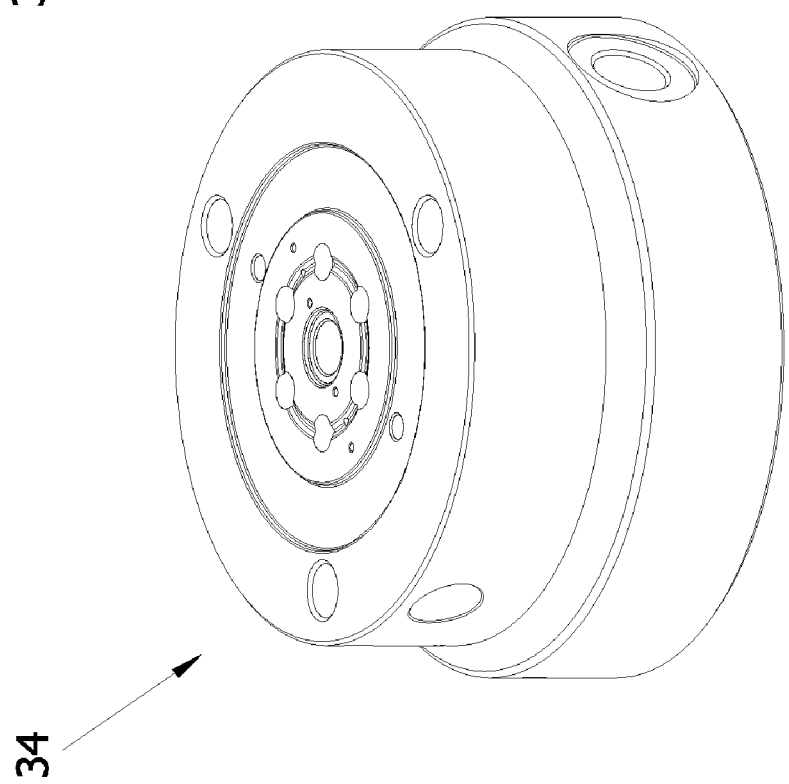
FIG. 15A is a top view of the valve body of the valve of FIG. 14.

In another embodiment, as shown in FIGS. 14A to 14B, the process purging channel 65 may be a groove 116, having for example a V-shape cross-section milled at a bottom of the main recess 60 of the valve body 34. Of course, the groove 116 may alternatively be U-shaped, square-shaped or have any other appropriate cross-section without departing from the scope of the present invention. In this other embodiment, the diaphragm 36 may sit directly at the bottom of the main recess 60, close-fitting its surface, the process purging channel 65 being the space defined by the second surface 76 of the diaphragm 36 and the surface of the groove 116. FIGS. 15A and 15B show the valve body of this other preferred embodiment, where the groove 116 forming the process purging channel 65 is shown.

Figure 7D:
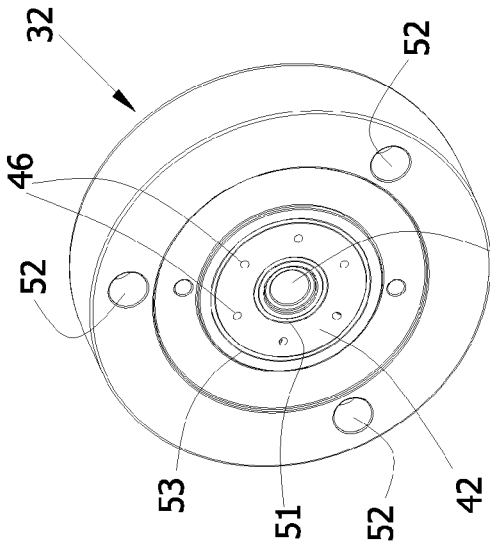
FIGS. 7D and 7E are a bottom perspective view and a top perspective view of the valve cap of FIG. 7, respectively.
Figure 7E:
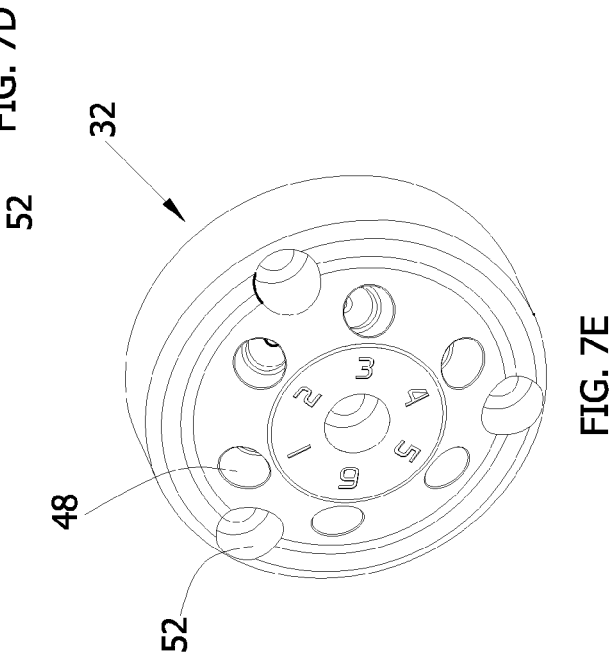
Figure 7B:
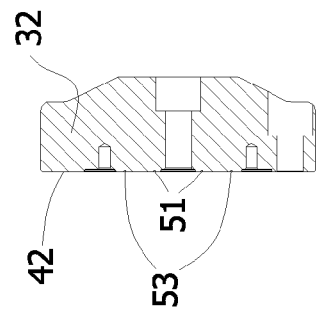
FIG. 7B is a cross-sectional side view of the valve cap along line B-B of FIG. 7A.
Figure 7A:
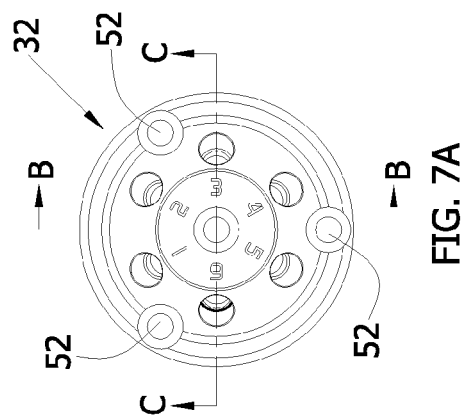
FIG. 7A is a top view of the valve cap of the valve of FIG. 2, according to a preferred embodiment of the present invention.
Figure 7C:
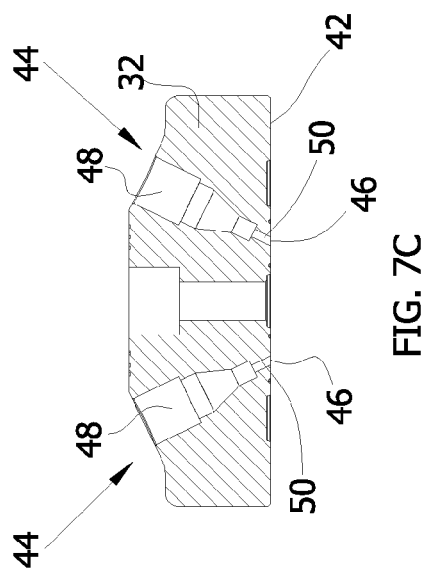
FIG. 7C is a cross-sectional view of the valve cap along the lines C-C of FIG. 7A.

Now referring to FIGS. 4 and 4B to 4D, and also to FIG. 7D, the valve 30 may comprise a purge circulation line to collect inboard and outboard leaks between the first interface 42 of the valve cap 32 and the first surface 74 of the diaphragm. This purge circulation line includes an outer annular channel 53 extending at the first interface 42 of the valve cap 32 outwardly of the process ports 46, an inner annular channel 51 also extending in the first interface 42 inwardly of the process ports 46 and a pair of fluid inlets 70 and the pair of fluid outlets 72, each pair having a first opening 84 in the inner annular channel 51 and a second opening 86 in the outer annular channel 53. The pair of fluid inlets 70, just like the process purging inlet passage 66 is connected to the entry 67 of a purge line, and the pair of fluid outlets 72, just like the process purging outlet passage 68, is connected the exit 69 of the purge line, for providing a continuous fluid flow in the outer 53 and the inner 51 annular channels, advantageously allowing inboard and outboard leaks to be vented or evacuated out of the valve 30.

Plunger Assembly

Referring to FIGS. 2 and 6, 6A and 6B, there is shown a preferred embodiment of a plunger assembly of the valve 30. In this preferred embodiment, the plunger assembly 38 (as indicated in FIG. 2) has a plurality of plungers 82, each placed in one of the passages 62 (more clearly shown in FIGS. 6A and 6B) of the valve body 34. The term "plunger" is understood to mean a mechanism component driven by or against a mechanical force or fluid pressure. The plungers 82 can slide in the passages 62, between a closed position and an open position. In the close position, the plunger 82 projects towards the first interface 42, and presses the diaphragm 36 against the first interface 42 of the valve cap 32, between two adjacent ports 46 for interrupting communication between these ports 46. In the open position, the plunger 82 is retracted within the valve body 34 and extends away from the diaphragm 36 for allowing communication between the two adjacent ports 46. Preferably, each plunger 82 of the plunger assembly 38 is either a normally closed plunger 82nc or a normally open plunger 82no. Still preferably, guide sleeves 81 surround the normally open plungers 82no, for facilitating the movement of the plungers into the passages. The left side plunger of FIG. 6 is shown in the closed position, whereas the right side plunger is shown in the open position. Of course, plungers may take other shapes than that of a cylinder, as long as they can be in an open position where communication between the two adjacent ports 46 is allowed, and a close position where communication between the two adjacent ports 46 is shut off. Other possible types of plungers 82 may include for example bearing balls.

Figure 10D:
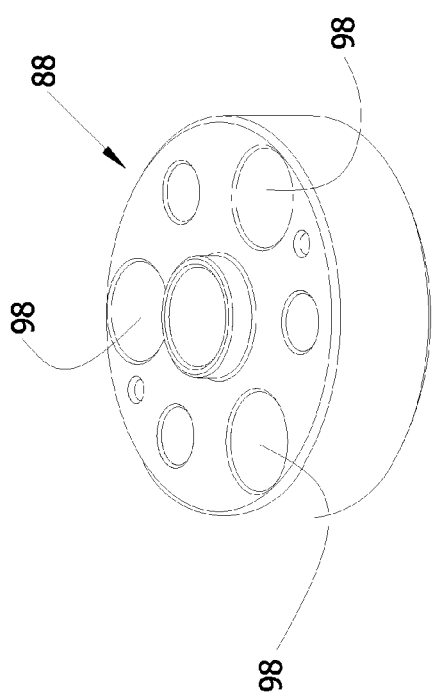
FIG. 10D is a top perspective view of the push plate of FIG. 10A.
Figure 10C:
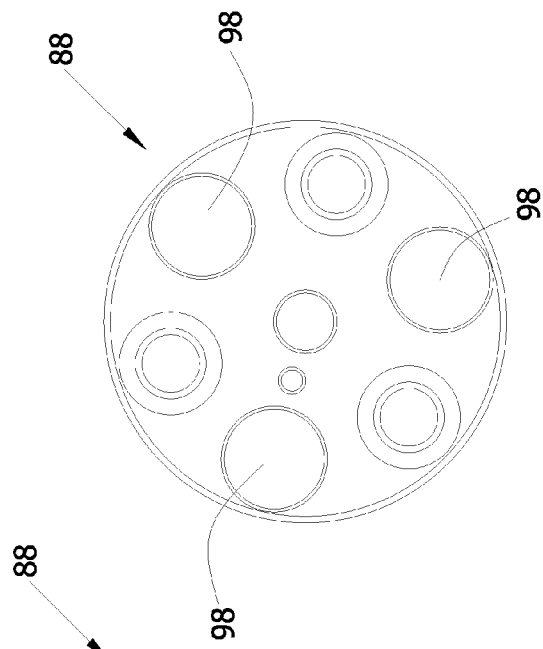
Figure 10B:
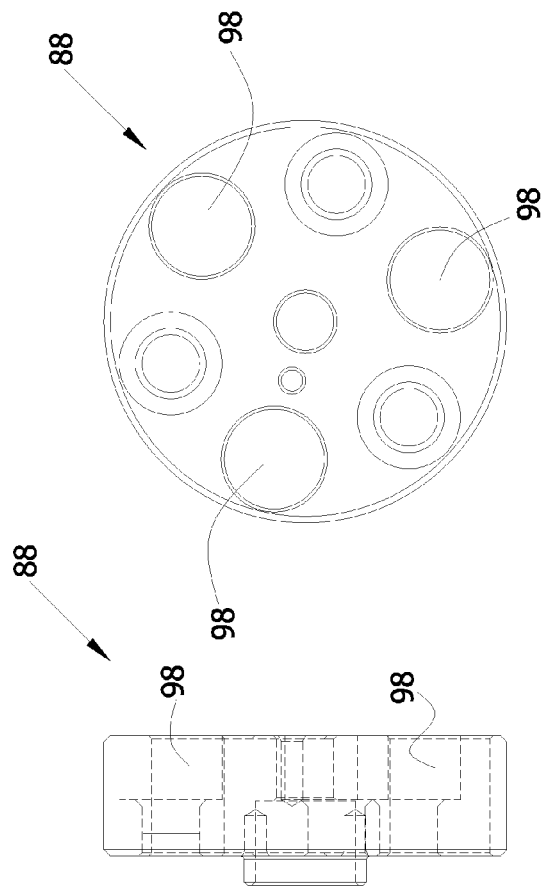
FIG. 10B is a side view of the push plate of FIG. 10A.
Figure 10A:
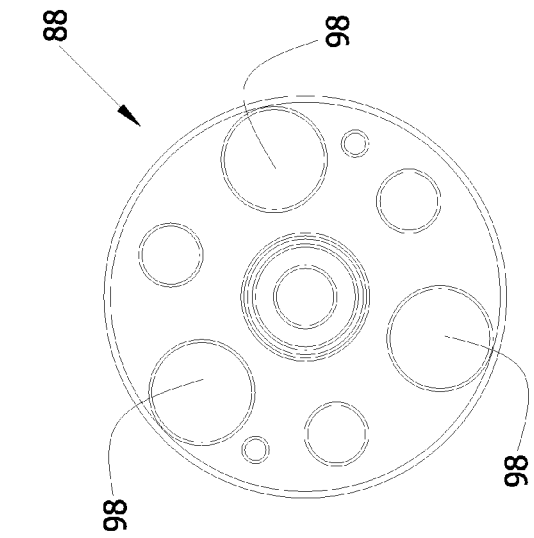
FIG. 10A is a top view of the push plate of the valve of FIG. 2, according to a preferred embodiment of the present invention.
Figure 11B:
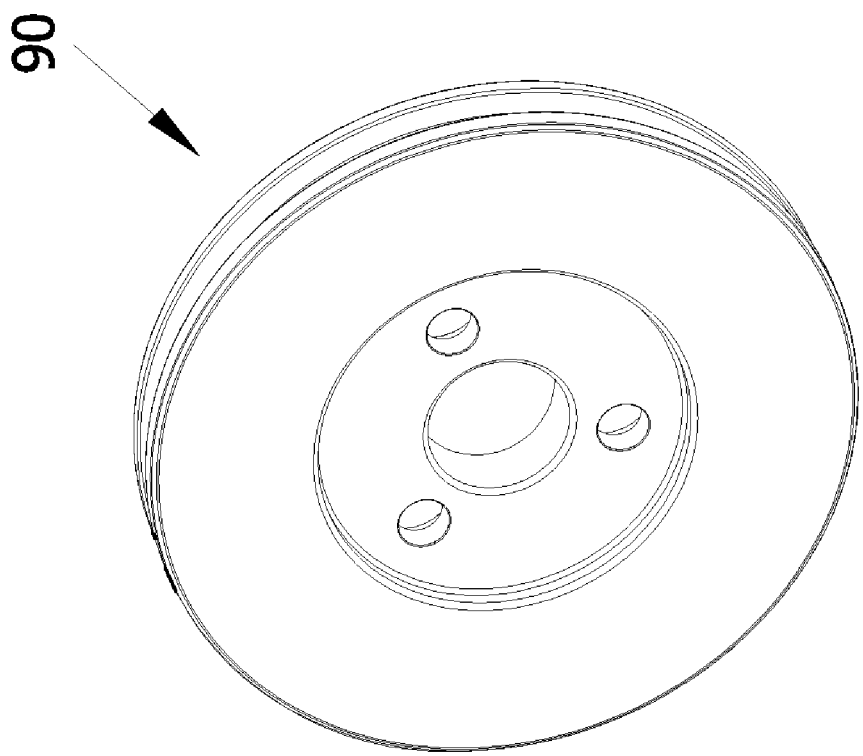
FIG. 11B is a top perspective view of the normally open piston of FIG. 2.
Figure 11A:
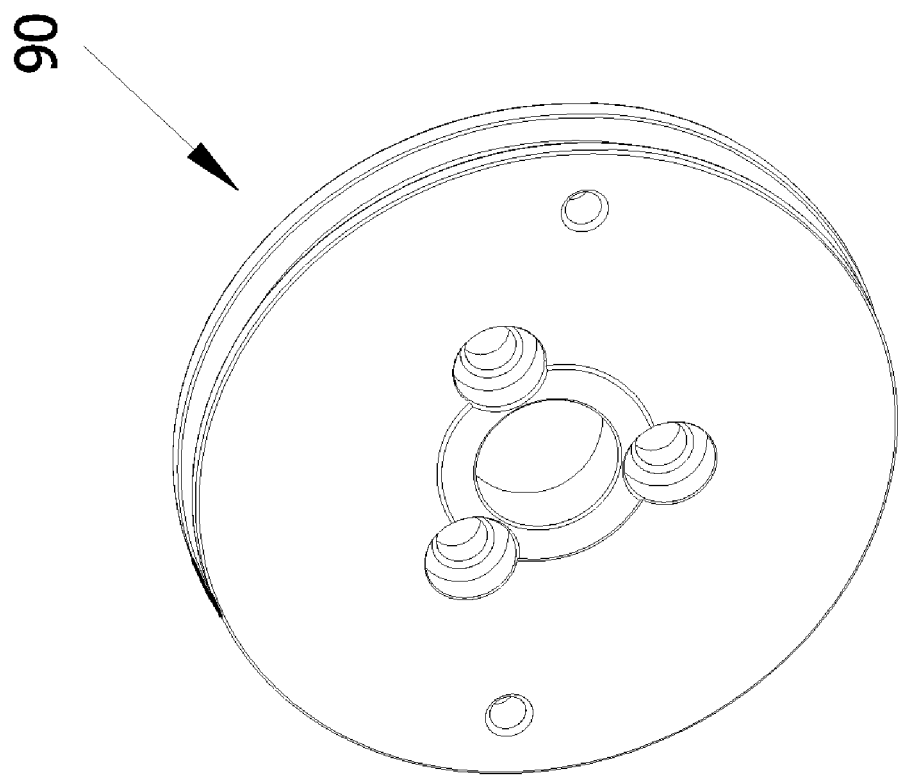
Figure 12B:
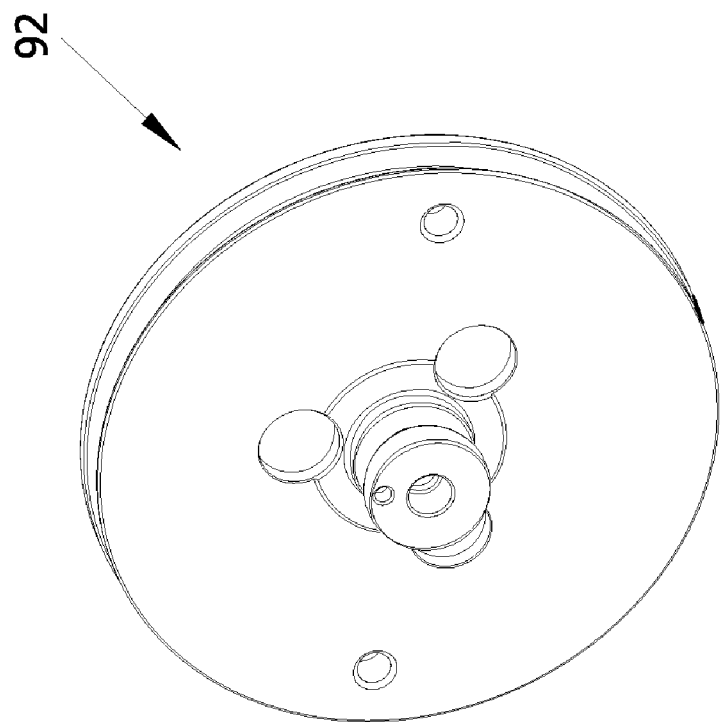
FIG. 12B is a top perspective view of the normally closed piston of FIG. 2.
Figure 12A:
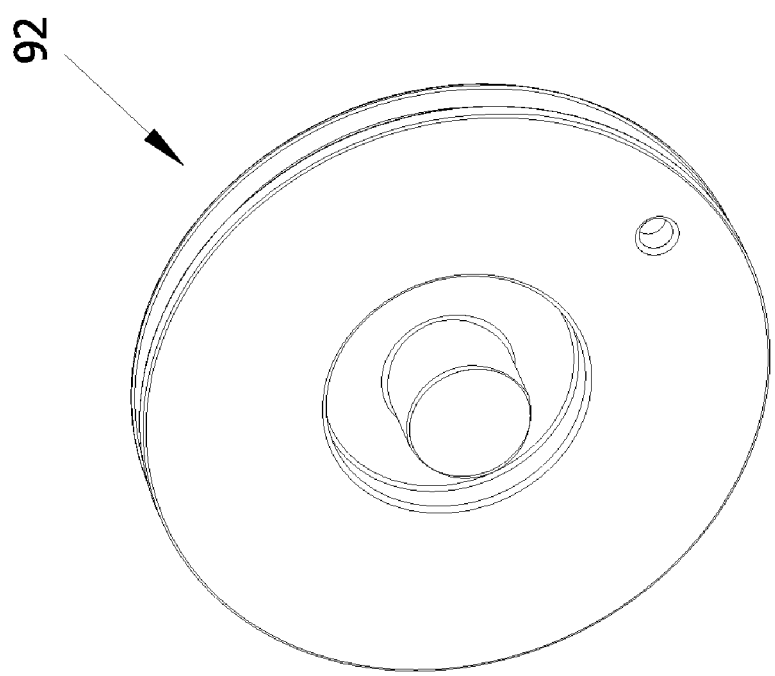
Figure 13B:
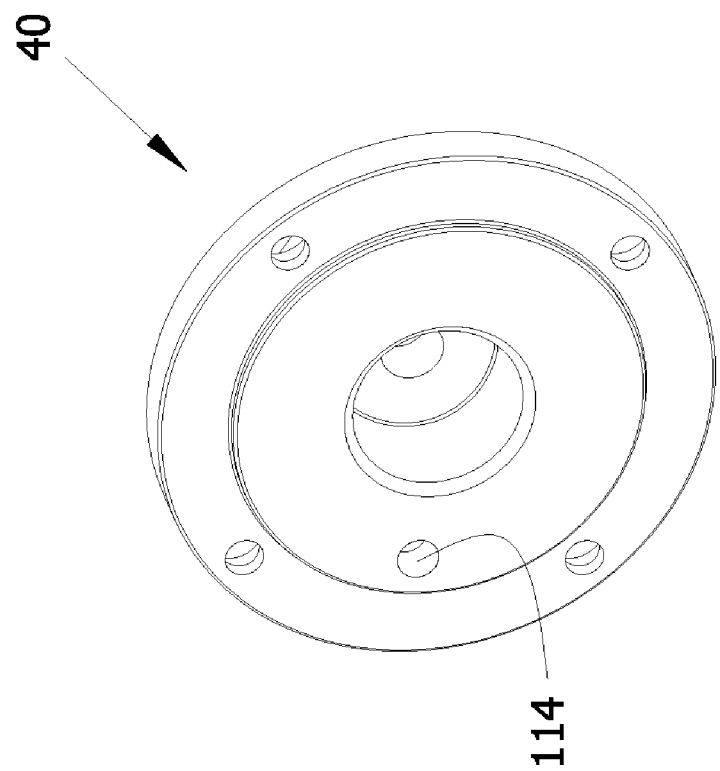
FIGS. 13A and 13B are a bottom perspective view and a top perspective view of the bottom cap of FIG. 2, respectively.
Figure 13A:
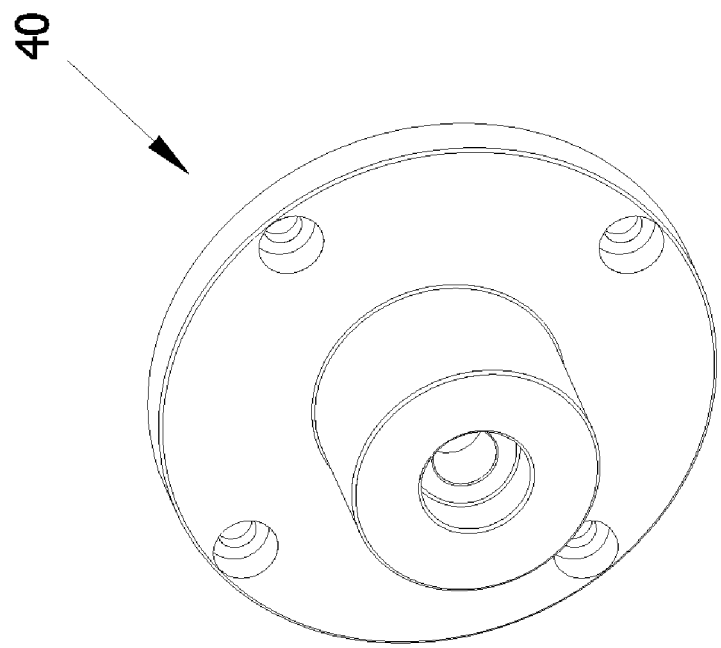

As shown in FIGS. 2, 5 and 6, the plunger assembly not only includes the plungers but also preferably have means for displacing the plungers into the passages 62. As illustrated, the plungers 82 are preferably actuated by a push plate 88, an upper piston 90, a lower piston 92, biasing means 94 and an actuating mechanism 96. The push plate 88 extends within the cavity 63 of the valve body 34, in parallel to the second interface 58 of the valve body. The push plate 88 is movable transversally to this second interface 58, or in other words in parallel to the central axis of the cylindrical valve body 34. The normally closed plungers 82nc are mounted on the push plate 88. A guide sleeve 81 surrounds the push plate 88 for facilitating its movement within the upper section of the cavity 63 of the valve body 34. A plurality of cavities 98 (shown in FIGS. 10A to 10C) extends across the push plate 88 for allowing the normally open plungers 82no to pass through it. The upper piston 90 extends contiguously under the push plate, the normally opened plungers 82no being placed on it. The lower piston 92 extends under the upper piston 90 contiguously to it, the lower piston 92 being rigidly connected to the push plate 88, preferably with a screw 54. O-rings 89 are preferably provided on the outline of each pistons, to properly seal the upper 94 and lower 90 pistons to the inner surface of the valve body 34. In this preferred embodiment, when either the upper 90 or lower pistons 92 are retracted, their corresponding plungers 82 attached thereto are pulled down, ensuring that it does not press against the diaphragm 36. Thus, with this particular design, the valve 30 can advantageously be mounted in any position, since there are no "floating" plungers. FIGS. 11A and 11B show more clearly the piston 90 of this preferred embodiment, while FIGS. 12A and 12B show more clearly the piston 92.

More clearly shown in FIGS. 2 and 4, biasing means 94 ensure that the lower piston 92 is upwardly biased and that the upper piston 90 is downwardly biased. Preferably, a Belleville washer 100 assembly cooperates with the lower piston 92 and a bottom cap screw 102 controls an upward force on the Belleville washer assembly 100. Still preferably, it is a disc spring 104 extending over the upper piston 90 that exerts a downward force on the upper piston 90 and therefore downwardly biases it.

Now referring to FIG. 5, to actuate the plungers, the actuating mechanism 96 controls a distance or space between the upper 90 and lower 92 pistons. In this preferred embodiment, it can be seen that the actuating mechanism 96 actuates the plungers 82 between the opened and closed positions, by injection of actuation gas between the upper 90 and lower 92 pistons, the actuating mechanism being pneumatic actuators.

Referring to FIGS. 2, 5, 5A and 5B, in order to avoid situations where an over pressurising of the actuator damages the diaphragm, the pistons 90, 92 are advantageously provided with some room there around to add shims 108 of various thicknesses. These shims 108 stop the piston travelling, since the piston will seat thereon. The idea is to use the right shim thickness for a particular application. These shims 108 are advantageously used on the normally open piston 90 (or upper piston), more clearly shown in FIG. 5B, but also on the pushed plate 88 which is connected to the normally closed piston 92, more clearly shown in FIG. 5A. However, it is important to note that the use of such shims 108 on the normally closed piston 92 is not intended to avoid damage when using a higher operating pressure to actuate the valve 30, since pressure is used to lift the pistons to open the fluid communication channel between two adjacent ports 46.

In fact, if the bottom cap set screw 110 is particularly adjusted in order to require a high pressure to lift the corresponding piston 90, 92, the result is that the time that all ports 46 are closed upon valve actuation will advantageously be longer, then eliminating even more the risk of cross port flow or the so called "mixing". This higher pressure operation will not cause damages since the corresponding piston stroke is limited by the shims stack. This provides a convenient way to adjust or to "time" the valve sequence operation by setting the step of "all ports closed" more or less longer.

Now referring to FIGS. 2, 5, 13A and 13B, the bottom cap 40 is affixed to the valve body, preferably with socket head cap screws 54, and it also house the bottom cap set screw 102 that allow adjustment of the pressure exerted on the normally closed piston 92 via the Belleville washer assembly 100. The bottom cap 40 is also advantageously provided with a bottom cap actuation vent 114 extending in it and located opposite to the actuating mechanism 96 of the plunger assembly 38, for preventing pressure build up between the lower piston 92 and the bottom cap 40.

Oftentimes, after diaphragm valves are built and fully tested, they are sealed in plastic packages, packed and stored in inventory before shipping to customers. Depending on various factors such as market demand, inventory management, customer need and the like, valves are likely to stay unused for weeks or months after their manufacture. In addition, in some circumstances a valve owner may temporarily shut down or remove a valve from active use for an undetermined amount of time before putting it in service again. While a valve is idle, its normally closed plungers are in their closed position and therefore apply a constant pressure on the diaphragm. Depending on diaphragm material, this could lead to a permanent deformation of the diaphragm, and reduced efficiency of the valve. A pressure relief mechanism may therefore be used to lock the normally closed plungers in their open position when the valve is not in use.

Figure 16A:
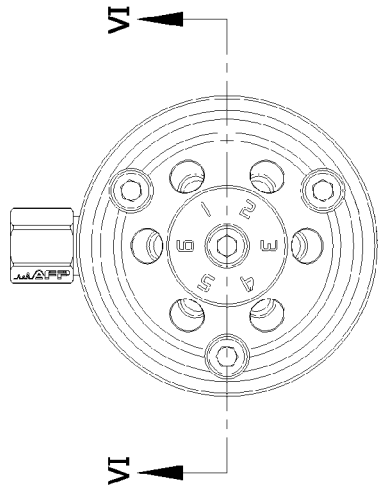
FIG. 16A is a top view of a diaphragm-sealed valve according to yet another preferred embodiment of present invention.
Figure 16C:
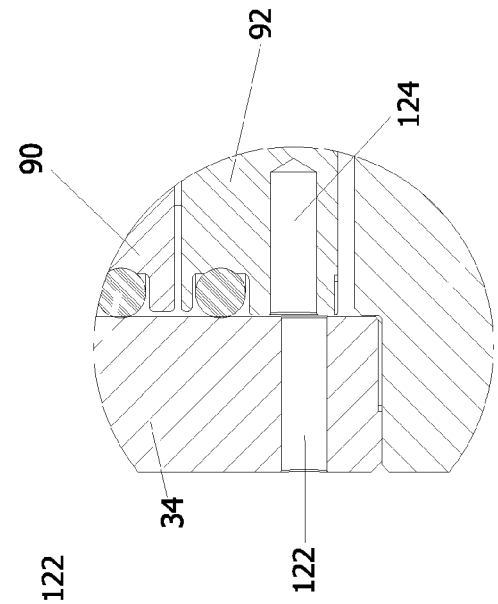
FIG. 16C is an enlarged view of section 16C of FIG. 16B.
Figure 16B:
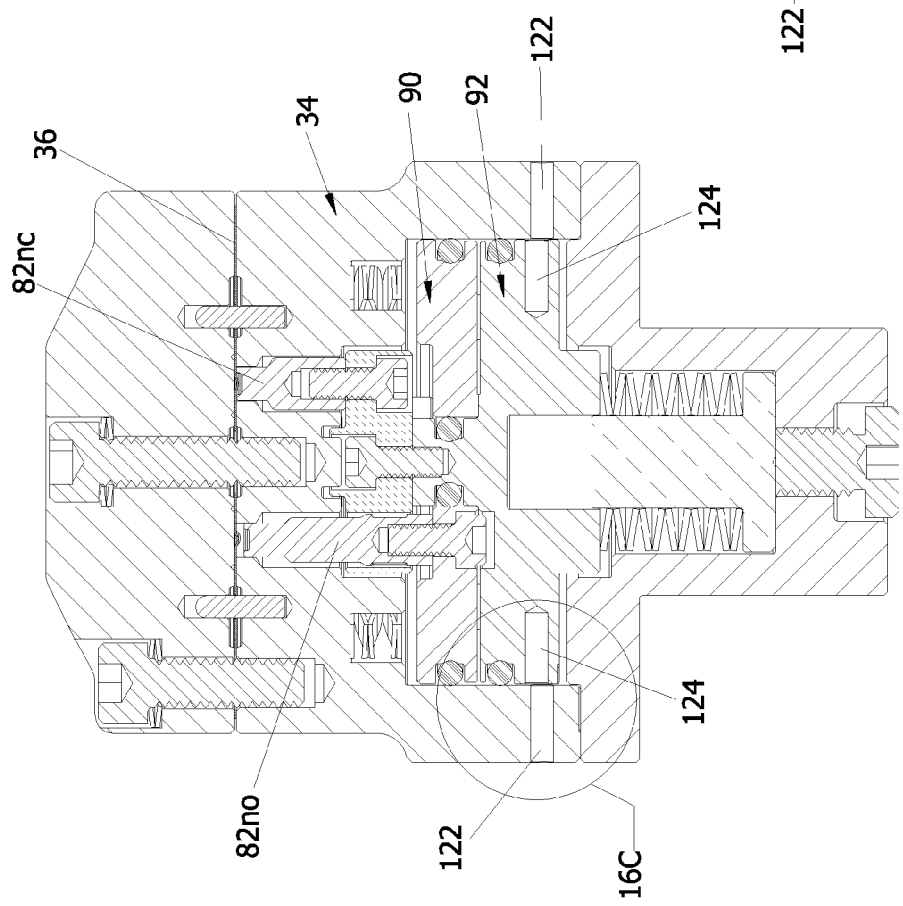
FIG. 16B is a cross-sectional side view of a diaphragm-sealed valve along line VI-VI of FIG. 16A.

As illustrated in the embodiment shown in FIGS. 16A to 16C, the valve body 34 preferably includes at least one transverse passage 122 extending therethrough from a side of the valve 30 to the lower piston 92. The lower piston 92 also includes such a transverse passage 124, which is aligned with the transverse passage 122 of the valve body 34 when the lower piston 92 is lowered, and the normally closed plungers 82*nc* therefore is in the open position.

Figure 17A:
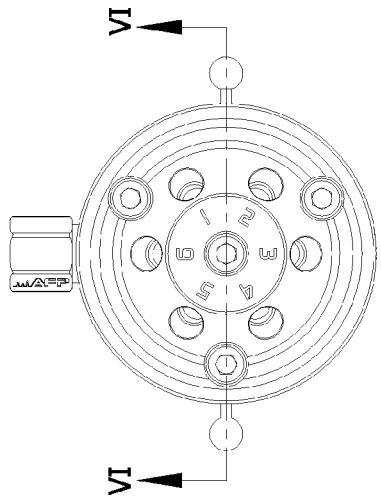
FIG. 17A is a top view of the diaphragm-sealed valve of FIG. 16A, with locking pins inserted.
Figure 17C:
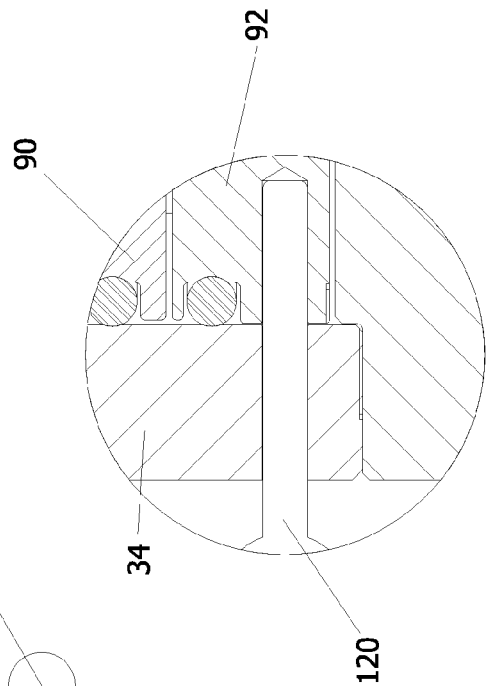
FIG. 17C is an enlarged view of section 17C of FIG. 17B.
Figure 17B:
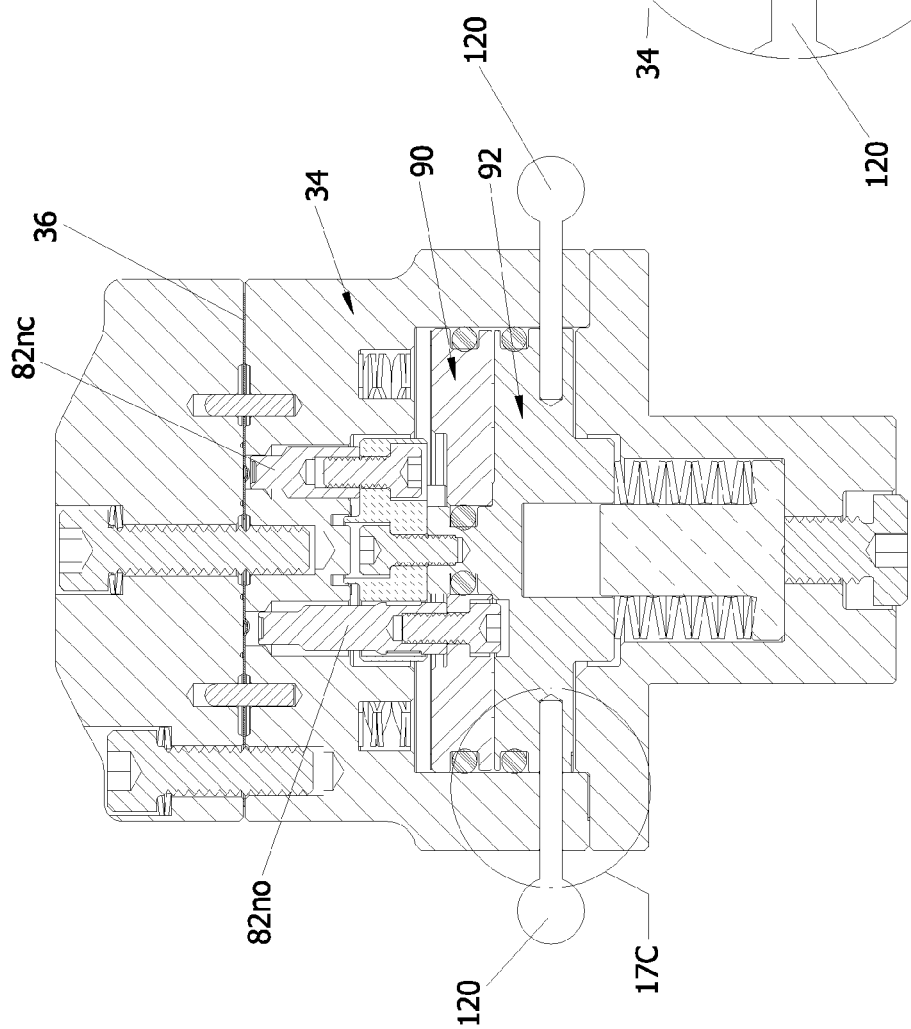
FIG. 17B is a cross-sectional side view of a diaphragm-sealed valve along line VI-VI of FIG. 17A.

Referring to FIGS. 17A to 17C, a locking pin 120 is provided and insertable through the aligned transverse passages 122, 124 of the valve body 34 and lower piston 92. In this illustrated embodiment, two sets of transverse passages 122, 124 and corresponding locking pins 120 are shown, but it will be understood that any number of passages 122, 124 and pins 120 may be provided. In order to lock the valve, the actuating mechanism 96 is operated to lower the normally closed piston 92, preferably by supplying pressurized gas between the upper 90 and lower 92 pistons as explained above. This brings the transverse passages 122, 124 of the valve body 34 and lower piston 92 in alignment, and the locking pin 120 can be inserted therein. Once the locking pin 120 is in place, the actuating mechanism 96 can be deactivated, and both the normally closed 82*nc* and normally opened 82*no* plungers will remain in their open position, leaving the diaphragm 36 free of mechanical stress thereon. The valve 30 can simply be reactivated and the locking pin 120 removed whenever the valve 30 needs to be used again.

Although preferred embodiments of the present invention have been described in detail herein and illustrated in the accompanying drawings, it is to be understood that the invention is not limited to these precise embodiments and that various changes and modifications may be effected therein without departing from the scope of the present invention.

The invention claimed is:

1. A valve comprising:
   a valve cap having a first interface and a plurality of process conduits extending therethrough, each process conduit ending in a process port opening at the first interface;
   a valve body having a second interface facing the first interface of the valve cap, the second interface being provided with a main recess aligned with said process ports, the valve body comprising a plurality of passages each extending in the valve body and opening in the main recess between two of the process ports;
   a diaphragm having a first surface facing the valve cap and a second surface facing the valve body, the diaphragm being compressibly positioned between the first and the second interfaces, the diaphragm having a pre-formed deformation lying within the main recess of the valve body, the first surface of the diaphragm defining with the first interface of the valve cap a communication channel between the process ports;
   a plunger assembly comprising a plurality of plungers each placed in one of said passages and being slideable therein between a closed position where said plunger projects towards the first interface pressing the diaphragm against the first interface of the valve cap between two adjacent ports for interrupting communication there between, and an open position where said plunger is retracted within said valve body, extending away from the diaphragm for allowing communication between the two adjacent ports;
   the valve body further comprising a process purging channel extending along the main recess under the pre-formed deformation of the diaphragm, a process purging inlet passage and process purging outlet passage, both opening on the process purging channel.

2. A valve according to claim 1, wherein the process purging channel is defined by the second surface of the diaphragm and a bottom of the main recess, the process purging channel having a semi-circular cross-section.

3. A valve according to claim 1, wherein the process purging channel comprises a groove extending at a bottom of the main recess of the valve body.

4. A valve according to claim 1, wherein the process purging inlet passage and the process purging outlet passage are diametrically opposed along said main recess.

5. A valve according to claim 1, wherein each plunger of the plunger assembly is either a normally closed plunger or a normally open plunger.

6. A valve according to claim 5, wherein the plunger assembly comprises:
   a push plate extending within the valve body in parallel to the second interface and movable transversally thereto, the normally closed plungers being mounted on said push plate, a plurality of cavities extending across said push plate for allowing the normally open plungers therethrough;
   an upper piston extending under the push plate contiguously thereto, the normally opened plungers being placed thereon;
   a lower piston extending under the upper piston contiguously thereto, the lower piston being rigidly connected to the push plate;
   biasing means for upwardly biasing the lower piston and downwardly biasing the upper piston; and
   an actuating mechanism for actuating the plungers between the opened and closed positions thereof, the actuating mechanism controlling a distance between the upper and lower pistons.

7. A valve according to claim 6, further comprising a bottom cap affixed to the valve body, said bottom cap being provided with an actuation vent extending therein and located opposite to the actuating mechanism of the plunger assembly, for preventing pressure build up between the lower piston and the bottom cap.

8. A valve according to claim 6, wherein the biasing means comprise a Belleville washer assembly cooperating with the lower piston and a screw for controlling an upward force on said Belleville washer assembly.

9. A valve according to claim 6, wherein the biasing means comprise a disc spring extending over the upper piston.

10. A valve according to claim 1, further comprising a purge circulation line comprising:
   an outer annular channel extending in the first interface outwardly of said process ports;
   an inner annular channel extending in the first interface inwardly of said process ports;
   a pair of fluid inlets and a pair of fluid outlets, each pair having a first opening in the inner annular channel and a second opening in the outer annular channel, for providing a continuous fluid flow in the outer and the inner annular channels, to collect inboard and outboard leaks from the valve, the pair of fluid inlets and the process purging inlet passage being connected to an entry of a purge line, and the pair of fluid outlets and the process purging outlet passage being connected to an exit of the purge line.

11. A valve according to claim 6, further comprising a purge circulation line comprising:
   an outer annular channel extending in the first interface outwardly of said process ports;
   an inner annular channel extending in the first interface inwardly of said process ports;
   a pair of fluid inlets and a pair of fluid outlets, each pair having a first opening in the inner annular channel and a second opening in the outer annular channel, for providing a continuous fluid flow in the outer and the inner annular channels, to collect inboard and outboard leaks from the valve, the pair of fluid inlets and the process purging inlet passage being connected to an entry of a purge line, and the pair of fluid outlets and the process purging outlet passage being connected to an exit of the purge line;
wherein the valve body further comprises an actuation purging outlet passage connected to the exit of the purge line, the actuation purging outlet passage extending in the valve body and located opposite to the push plate of the plunger assembly, for preventing pressure build up between the push plate and the valve body.

12. A valve according to claim 1, further comprising a layer of a polymer covering the first interface of the valve cap.

13. A valve according to claim 1, wherein the diaphragm comprises multiple layers made of a polymer, multiple layers of polymer covered with a layer of metal or multiple layers of metal.

14. A valve according to claim 1, wherein the valve cap comprises six of said process ports and the plunger assembly comprises six of said plungers, wherein the process ports are circularly arranged on the first interface and wherein two adjacent plungers comprise a normally closed plunger and a normally open plunger.

15. A valve according to claim 14, wherein the main recess is circular.

16. A method for collecting leaks from a communication channel in a valve, the valve having:
   a valve cap having a first interface and a plurality of process conduits extending therethrough, each process conduit ending in a process port opening at the first interface;
   a valve body having a second interface facing the first interface of the valve cap, the second interface being provided with a main recess aligned with said process ports, the valve body comprising a plurality of passages each extending in the valve body and opening in the main recess between two of the process ports;
   a diaphragm having a first surface facing the valve cap and a second surface facing the valve body, the diaphragm being compressibly positioned between the first and the second interfaces, the diaphragm having a pre-formed deformation lying within the main recess of the valve body, the first surface of the diaphragm defining with the first interface of the valve cap the communication channel between the process ports;
   a plunger assembly comprising a plurality of plungers each placed in one of said passages and being slideable therein between a closed position where said plunger projects towards the first interface pressing the diaphragm against the first interface of the valve cap between two adjacent ports for interrupting communication there between, and an open position where said plunger is retracted within said valve body, extending away from the diaphragm for allowing communication between the two adjacent ports;
   the valve body further comprising a process purging channel extending along the main recess under the pre-formed deformation of the diaphragm, a process purging inlet passage and process purging outlet passage, both opening on the process purging channel;
said method comprising the steps of:
   a) providing the valve body with a process purging channel extending along the main recess under the pre-formed deformation of the diaphragm, a process purging inlet passage and a process purging outlet passage, both opening on the process purging channel;
   b) circulating purging gas in the process purging channel from the process purging inlet passage to the process purging outlet passage.

* * * * *